United States Patent [19]
Blades et al.

[11] Patent Number: 5,275,957
[45] Date of Patent: * Jan. 4, 1994

[54] INSTRUMENT AND METHOD FOR MEASUREMENT OF THE ORGANIC CARBON CONTENT OF WATER

[75] Inventors: Frederick K. Blades; Paul C. Melanson, both of Boulder; Richard D. Godec, Erie, all of Colo.

[73] Assignee: Anatel Corporation, Boulder, Colo.

[*] Notice: The portion of the term of this patent subsequent to Sep. 19, 2006 has been disclaimed.

[21] Appl. No.: 757,327

[22] Filed: Sep. 10, 1991

Related U.S. Application Data

[63] Continuation-in-part of Ser. No. 270,451, Nov. 7, 1988, Pat. No. 5,047,212, which is a continuation of Ser. No. 938,634, Feb. 19, 1987, abandoned, which is a continuation of Ser. No. 635,551, Aug. 2, 1984, Pat. No. 4,666,860, which is a continuation-in-part of Ser. No. 569,678, Jan. 10, 1984, Pat. No. 4,626,413.

[51] Int. Cl.$^5$ ............................................. G01N 31/12
[52] U.S. Cl. ................................... 436/133; 436/146; 436/150; 436/905; 436/159; 422/82.02; 422/82.12; 422/78; 422/186.3
[58] Field of Search ............................. 422/68, 78–80; 436/62, 146, 150, 905, 133, 159; 250/372, 373, 435; 356/51

[56] References Cited

U.S. PATENT DOCUMENTS

| | | |
|---|---|---|
| 2,019,871 | 11/1935 | Pettingill et al. |
| 3,224,837 | 12/1965 | Moyat |
| 3,287,088 | 11/1966 | Seevers |
| 3,535,087 | 10/1970 | Hart et al. |
| 3,607,071 | 9/1971 | Staffin et al. |
| 3,738,812 | 6/1973 | Berry et al. |
| 3,854,877 | 12/1974 | Csaky et al. |

(List continued on next page.)

FOREIGN PATENT DOCUMENTS

| | | |
|---|---|---|
| 3117537 | 5/1981 | Fed. Rep. of Germany |
| 3223167 | 12/1983 | Fed. Rep. of Germany |
| 2029015 | 3/1980 | United Kingdom |

OTHER PUBLICATIONS

Poirier et al "A New Approach to the Measurement of Organic Carbon", American Laboratory, Dec. 1978, pp. 1–8.

(List continued on next page.)

Primary Examiner—James C. Housel
Assistant Examiner—Jeffrey R. Snay
Attorney, Agent, or Firm—Michael de Angeli

[57] ABSTRACT

Apparatus and methods for measurement of total organic carbon content of water, particularly of low relative organic content, are described, featuring a single sample cell for exposure of a static sample to ultraviolet radiation and comprising electrodes for measuring the conductivity of the water. The conductivity is monitored as a function of time and the second time derivative of the conductivity signal is monitored to indicate when the oxidation reaction has been completed. Compensation for the contribution to conductivity of the water sample made by the instrument is achieved by subtracting a quantity proportional to the first time derivative of the conductivity at a time when the second time derivative reaches zero, indicating that the oxidation reaction is complete, from the change in the total conductivity measurement, the remainder being equal to the contribution to conductivity made by oxidation of the organic content of the water. The electrodes may have surfaces of a material which when irradiated by the ultraviolet radiation catalyzes the oxidation reaction. Electrophoresis may also be employed to speed the reaction. In appropriate cases, the pH of the water sample is additionally measured and used together with the temperature of the sample to derive a series of values for the carbon dioxide content of the sample from the measured values of the conductivity. For further accuracy, the actual carbon dioxide content values may be employed in the analysis in lieu of the conductivity values.

46 Claims, 14 Drawing Sheets

U.S. PATENT DOCUMENTS

| | | |
|---|---|---|
| 3,955,924 | 5/1976 | Northmore et al. . |
| 3,958,941 | 5/1976 | Regan . |
| 3,964,868 | 6/1976 | DiCola et al. . |
| 4,140,018 | 2/1979 | Maldarelli et al. . |
| 4,227,151 | 10/1980 | Ellis et al. . |
| 4,248,598 | 2/1981 | Blunck . |
| 4,272,679 | 6/1981 | Blades . |
| 4,288,229 | 9/1981 | Mar . |
| 4,293,522 | 10/1981 | Winkler . |
| 4,304,996 | 12/1981 | Blades . |
| 4,357,668 | 11/1982 | Schwartz et al. . |
| 4,418,566 | 12/1983 | Beck et al. . |
| 4,523,331 | 6/1985 | Asija . |
| 4,566,073 | 1/1986 | Zwicke . |
| 4,626,413 | 12/1986 | Blades et al. ............... 422/82.02 X |
| 4,666,860 | 5/1987 | Blades et al. ...................... 436/146 |
| 4,683,435 | 7/1987 | Blades . |
| 4,749,657 | 6/1988 | Takahashi et al. . |
| 4,769,217 | 9/1988 | Sienkiewicz et al. .......... 436/146 X |
| 4,868,127 | 9/1989 | Blades et al. . |
| 5,047,212 | 9/1991 | Blades et al. ...................... 436/146 |
| 5,141,717 | 8/1992 | McRae ............................ 436/146 X |

OTHER PUBLICATIONS

Sybron brochure, PHOTOchem Organic Carbon Analyzers, Analytical Products, Boston, MA.

"Organic Heterogeneous Photocatalysis: Chemical Conversions Sensitized by Irradated Semiconductors", Fox, Acc. Chem. 16, 314–321 (1983).

Arakawa, "The Present Status and Trends of Photocatalytic Reactions", *Techno Japan,* vol. 18, No. 11, Nov. 1985, pp. 9–22.

Bard, "Photoelectrochemistry and Heterogeneous Photocatalysis at Semiconductors", *J. Photochemistry* 10 (1979) pp. 59–75.

Symanski et al, "Conductometric Sensor for Atmospheric Carbon Dioxide Determination", American Chemical Society, 1983, 55, pp. 1152–1158.

INSTRUMENT AND METHOD FOR MEASUREMENT OF THE ORGANIC CARBON CONTENT OF WATER

CROSS REFERENCE TO RELATED APPLICATIONS

This application is a continuation-in-part of Ser. No. 07/270,451, filed Nov. 7, 1988, now U.S. Pat. No. 5,047,212 issued Sep. 10, 1991, which was a continuation of Ser. No. 06/938,634, filed Feb. 9, 1987, now abandoned, which was a continuation of Ser. No. 635,551, filed Aug. 2, 1984, now U.S. Pat. No. 4,666,860, which was a continuation-in-part of Ser. No. 569,678 filed Jan. 10, 1984, now U.S. Pat. No. 4,626,413.

FIELD OF THE INVENTION

This invention relates to instruments for the measurement of the total organic carbon (TOC) content of water. More particularly, the invention relates to instruments for accurately measuring low levels of organic carbon in substantially pure water streams.

BACKGROUND AND OBJECTS OF THE INVENTION

Modern high technology manufacturing processes often use highly purified "ultrapure" water in large quantities. The semiconductor industry in particular uses ultrapure water as a universal solvent in virtually every step of the production of integrated circuits. In recent years, it has been recognized that even trace amounts of organic contamination in the water, though often undetectable by the commonly-used ionic (i.e. conductivity-based) measurement techniques, can severely degrade both product quality and yield. Accurate and continuous monitoring of the total organic content is crucial if these problems are to be avoided. Similar problems exist through other industries, such as pharmaceutical and chemical manufacturing.

Several approaches to measurement of the organic content of water have been proposed. Those relevant to the present invention are primarily concerned with oxidation of the carbon in the organic material to carbon dioxide and then measuring the carbon dioxide content. This has been done in the past in several ways. The fact that carbon dioxide is an absorber of infrared light has been utilized. The oxidation has also been performed in several ways, including combustion, and using chemical oxidizers such as perchlorates. These methods are clumsy and are replete with the potential for significant errors, particularly in the low-TOC area addressed by the present invention. More relevant to the present invention is the approach shown in U.S. Pat. No. 3,958,941 to Regan, in which ultraviolet light is used to oxidize the carbon-containing organics in a water sample to carbon dioxide. (As a practical matter, in use of the Regan apparatus, the pH of the water sample is adjusted if necessary to ensure that the $CO_2$ is gaseous). The carbon dioxide is then transported to a pure water sample, in which the $CO_2$ is ionized, as $H^+$ and $CO_3^{--}$ ions. The change in conductivity of the pure water due to the presence of the additional ionic species is monitored to determine the amount of organic material thus oxidized. Oxidation of the organics to $CO_2$ and measurement of the change in the water's conductivity are used by the apparatus of the present invention. However, several improvements over the Regan apparatus are shown herein.

The Regan apparatus, which is commercially available, is proposed as a tool for measuring organic content of water over a wide range, from the parts per million (ppm) range through parts per thousand and, indeed, even higher. Applicants have had experience with this apparatus, however, and find that the problems inherent in total organic carbon measurement at extremely low dissolved organic levels, on the order of one part per billion (ppb) to one ppm are such that a different type of apparatus should be used for these extremely low level measurements. Thus, while the Regan approach is workable, it is of primary utility in the areas of relatively high organic concentrations.

The Regan apparatus requires the operator to perform several independent preliminary measurement runs to determine the "instrument contribution" or background level of the instrument. The inventors have found that the values determined in such measurements tend to change with time, thereby requiring frequent "calibration" runs to maintain measurement accuracy.

It is therefore an object of the invention to provide a means whereby the instrument contribution can be accurately determined separately from the measured quantity, such that calibration runs are eliminated.

The Regan apparatus assumes a fixed time for the oxidation process to go to completion. If the organics present in the sample are difficult to oxidize, or if the ultraviolet lamp has aged so as to produce insufficient oxidizing radiation, they may not be completely oxidized in the time allotted, thus leading to misleadingly low measurements. Furthermore, if the level of organics is very low and oxidation proceeds to completion rapidly, the interference caused by instrument contribution may contribute significant errors.

It is therefore a further object of the invention to provide an instrument whereby the oxidation process can be monitored so that its actual completion can be accurately and readily determined.

As mentioned, the Regan apparatus provides a two-loop system. The organics in a water sample are first oxidized by exposure to ultraviolet (UV) light, and the resulting carbon dioxide is transferred to a measurement chamber, and dissolved in pure water. The conductivity of the pure water is thereafter measured. The conductivity is thus measured in a different chamber than the chamber wherein the ultraviolet light is exposed to the water. This has the highly significant defect that transport of the carbon dioxide between the UV exposure chamber to the conductivity measurement chamber is obviously required. The present invention is designed to address measurement of the organic content of water in such low concentrations that any minor impurities added to the water by this or any comparable transport system (as well as loss of $CO_2$) can very greatly affect the accuracy of any measurement.

Accordingly, it is an object of the invention to provide an instrument for the measurement of total organic carbon in water which avoids water, $CO_2$ or other material handling or manipulative steps, such that the impurities inevitably added in such steps are avoided.

The present invention overcomes the problems associated with the defects of the Regan apparatus due to its transport and manipulative step requirements by providing a single chamber wherein the ultraviolet radiation is exposed to the water and conductivity measurements are made. Employment of a single chamber for both UV exposure and conductivity measurement has several advantages, including reduction of pollutants or contamination due to transport, simplicity, and low cost. Furthermore, the fact that the electrodes can be and are in a preferred environment exposed directly to the UV light means that there is no or very little chance of organic fouling of the electrodes, another problem inherent in the Regan apparatus according to the two-chamber approach proposed thereby.

It is accordingly an object of the invention to provide an instrument for measurement of total organic carbon in water in which a static water sample is measured for background conductivity, is then exposed to ultraviolet light, and variation in its conductivity is measured over time, without movement from a single sample chamber, whereby inaccuracies due to manipulative steps are eliminated.

It is a further object of the invention to provide such an organic matter measurement instrument in which the electrodes used for conductivity measurement are directly exposed to the ultraviolet light used to oxidize the organic carbon to carbon dioxide, such that organic fouling of the electrodes is avoided.

It is a further object of the invention, in accordance with good design practice, to avoid use of materials in contact with the water sample which could lead to leaching of additional impurities, such as iron, polyethylene and other materials found in prior designs, and instead to permit only relatively inert materials such as titanium or quartz to come into contact with the water sample.

As mentioned above, according to the invention, it is desired that a static water sample be examined; that is, according to the invention, a water sample is taken from the process of interest. The testing according to the invention is thus not an in-line process, as that term is typically used, although, in fact, the time taken for a typical measurement, on the order of one to twenty minutes, is such that substantially up-to-date information can be provided. (Note however that in some circumstances, detailed below, the apparatus of the invention can be used to monitor sudden changes in total organic carbon content in an in-line, real-time manner). The art generally teaches away from such static measurements, because it is known that the materials comprising the electrodes used for the resistive measurements as well as those of the sample chamber tend to be leached out into the water stream and make some contribution to the conductivity of the water. The more delicate the measurement, the more serious these contributions can be. Use of a flowing water stream has been suggested to minimize the effects of such additional ions which alter the conductivity.

It is a further object of the invention to provide a means by which the instrument contribution or "background" conductivity can be accurately determined and subtracted from the total measured value for conductivity, thus permitting use of a static sample measurement technique.

According to the present invention, accurate compensation is made for the instrument contribution due, e.g., to its materials leaching over time, so that the other advantages of static measurement can be realized, and so that the instrument contribution to conductivity, regardless of its source, is prevented from interfering with accurate measurement.

As mentioned, according to the process of the Regan patent, the conductivity of the water in a measurement chamber is first measured. The water sample of interest is exposed to ultraviolet light in a second exposure chamber for a fixed length of time. The carbon dioxide is then removed and dissolved into the water in the measurement chamber. The conductivity of the water is then measured and compared to its conductivity at the beginning of the exposure period. The difference is taken to be indicative of the change in conductivity due to $CO_2$ formed by oxidation of organic carbon. Because the relationship of conductivity of water to carbon dioxide content is known, this can be used to directly derive a measurement of organic carbon content. There are several difficulties inherent in this approach. One is that the background noise or instrument contribution, including the additional conductivity caused by leaching of organic or inorganic materials of the apparatus, is not repeatable over time, a fact brought out by the inventors' experiments. Furthermore, the dependence of conductivity of water on carbon dioxide content is not a linear function, but is exponential, such that at higher organic carbon contents, relatively little conductivity change is experienced with significant variation in organic carbon content. Hence, accurate determination of the background level is essential if an accurate measurement of organic content is to be provided.

Accordingly, it is an object of the invention to provide a method and instrument for measurement of the organic content of water accurately compensating for background and is made, wherein the compensation (a) is not dependent on repeatability of background measurement, (b) compensates in a simple and reliable manner for any chemical activity of the sample chamber or apparatus caused by ultraviolet light, and (c) is sufficiently delicate that the precision of result necessary for distinguishing between conductivity caused by various relatively low amounts of organic content is made possible.

One primary difficulty with prior art TOC measuring instruments is that all presently available devices require frequent and tedious calibration, due largely to the high and somewhat varying instrument contribution or background.

Accordingly, it is an object of the invention to provide a TOC measuring instrument, the absolute calibration of which is made solely by correctly calibrating an integral temperature-corrected conductivity sensor.

It is a further object of the invention to provide a TOC measuring instrument which automatically detects and compensates for such spurious background, substantially eliminating the need for frequent calibration.

THE FIRST CONTINUATION-IN-PART APPLICATION

After filing of application Ser. No. 569,678, now U.S. Pat. No. 4,626,413, it was realized that the sample cell design discussed therein could be improved. For one, the Teflon (trademark E. I. DuPont deNemours & Co.) material used for part of the cell deteriorates upon application of ultraviolet radiation. Further, the electrode design shown was not optimal with respect to uniformity of detection of ionic concentration in the water sample. Additionally, it was desired to have the cell withstand higher pressures.

After the filing of Ser. No. 569,678, now U.S. Pat. No. 4,626,413, it also became clear that in the case of certain oxidation reactions, intermediate products were being formed which had relatively higher conductivities than the ultimately-formed $CO_2$. This required modification of the data processing schemes employed to determine accurate TOC values.

Another discovery was that in monitoring the TOC content of a succession of water samples taken from the same process at intervals over a period of time, it was not always necessary to monitor the entire oxidation process in order to arrive at an accurate result. This is because if the initial portion of the conductivity versus time curve closely tracks that of a previous sample, it can be assumed that the final portion of the curve will do likewise. This permitted reduction of the time required to produce TOC output data.

Other aspects and objects of the improvements made according to the invention described in the first continuation-in-part application, Ser. No. 635,551, now U.S. Pat. No. 4,666,860, and the improvements disclosed and claimed in a second continuation-in-part Ser. No. 938,638, now U.S. Pat. No. 4,868,127, will appear as the discussion proceeds. However, many of the aspects and objects of both prior applications remain; in particular, accurate total organic carbon determination through a simple, single sample evaluation. Similarly, it is desired that there be no transport or manipulative steps required, that no chemicals or other oxidizers be added to the sample, that the cell design be such that the electrodes are exposed to the ultraviolet light to prevent fouling, and that the system is capable of providing accurate TOC data with respect to a wide variety of sources of organic matter.

THE SECOND CONTINUATION-IN-PART APPLICATION

In experiments with the instrument described according to the prior applications, certain surprising results and additional uses of the invention became apparent. In order that these could be fully disclosed and claimed, a second continuation-in-part application Ser. No. 938,638, now U.S. Pat. No. 4,868,127, was prepared and presented. The apparatus described in the prior applications, particularly the preferred embodiment thereof shown in Ser. No. 635,551 was suitable for employment of this new knowledge. Therefore, the discussion of these discoveries follows the discussion of the instrument itself, which is essentially as found in Ser. Nos. 569,678 and 635,551.

SUMMARY OF THE INVENTION

The present invention achieves the needs of the art and objects of the invention mentioned above by its provision of an instrument for the measurement of the total organic carbon content of water. The instrument comprises a single sample cell with two electrodes exposed directly to incident ultraviolet light. The temperature-corrected conductivity of the water is measured to establish a background value with no incident UV light, and then the UV lamp is switched on, exposing the sample to oxidizing radiation. The temperature-corrected conductivity of the water is measured and recorded over time. In a preferred embodiment, a dedicated computer device is used to monitor changes in the conductivity of the water over time. The computer is used to separate the changes in conductivity due to production of $CO_2$ from changes due to background instrument contributions. The method of differentiation of conductivity caused by background contamination from oxidized organics producing $CO_2$ is based on the relative state of completion of the two processes.

In the case of oxidation of organics in solution, the process is brought to completion within a short period of time e.e., one to twenty minutes. It is therefore a substantially non-linear function, asymptotically approaching its final value in a relatively short period of time.

The background contamination, on the other hand, is to a degree a function of extremely small quantities of contaminants diffusing into the sample during the oxidation period, thus producing a gradual increase in sample conductivity not related to the production of $CO_2$. Since the level of contaminants diffusing during this oxidizing period is likely several orders of magnitude below saturation, the conductivity contribution during this time is substantially linear and can therefore be mathematically differentiated from the non-linear production of $CO_2$. Other mechanisms such as diffusion of the $CO_2$ into or out of the cell may also add to the instrument contribution; it appears that these too do not reach equilibrium in the relatively short period of time during which the oxidation reaction is completed, and are linear during that period. Differentiation between the linear instrument contribution and the non-linear oxidation contribution is accomplished by observing the second time derivative of the conductivity of the water. When the second derivative becomes zero, within a predetermined measurement accuracy limit, this indicates that the oxidation reaction has been completed. The first time derivative of conductivity is also monitored; its value at the time the second derivative reaches zero is the "slope" of the background conductivity curve, due to the instrument contribution, and can be used to derive an indication of the total background noise, which can then be subtracted from the measured change in conductivity, such that the remainder is the conductivity resulting from the oxidation of the carbon present in the sample to $CO_2$.

According to an aspect of the invention of the first continuation-in-part application, now U.S. Pat. No. 4,666,860, it was recognized that several classes of oxidation processes must be accounted for. In particular, it was realized that some organics are oxidized to carbon dioxide only after passing through intermediate stages which have higher conductivity than the final product. Hence, means must be provided to identify such cases and to make accurate compensation. This can be done by monitoring the second time derivative of the conductivity curve in a matter generally similar to that previously defined.

It has also been realized that in cases of such relatively complex oxidation reactions, it may take as much as 15 to 20 minutes for the oxidation to be completed. While this is not in itself an insuperable obstacle to the utility of the apparatus of the invention, clearly it would be desirable to provide a shorter sampling period where possible. It has been realized that when monitoring the total organic carbon content of water samples from the same process stream taken at intervals over a period of time, conductivity data versus time curves are essentially very similar from sample to sample, unless the total organic carbon content suddenly changes. Hence, it is possible to conclude with certainty that the final total organic carbon content value of a given sample will be substantially the same as that measured with respect to previous samples, as long as the departure of the initial conductivity values form those previously recorded is within a predetermined limit. This fact can be effectively used to speed up repetitive monitoring of the total organic carbon content.

According to the invention of the second continuation-in-part application, now U.S. Pat. No. 4,868,127, it has been realized that a thin layer of titanium dioxide ($TiO_2$), formed on the titanium electrodes in the cell by oxidation of their surfaces, appears to provide a catalytic effect, speeding the oxidation of organics in the water to $CO_2$. This has the surprising effect that the organic contents of deoxygenated water streams, such as are commonly found in connection with power plants and the like, can be effectively measured using the techniques of the invention. It appears that the $TiO_2$ surface, when irradiated by ultraviolet radiation, causes the molecules of the water to break into OH radicals and $H_2$ molecules. At the same time, OH ions from the autodisassociation of water are attracted to the surface of the $TiO_2$ electrodes. The ultraviolet radiation irradiates the $TiO_2$ surface and a "photoelectrochemical" effect causes the electron from the $OH^-$ ion to be pumped away into the $TiO_2$ surface, leaving a highly oxidative OH radical. When the organics initially break up in the water, due to the influence of the ultraviolet light thereon, they break into ionic species, typically acetic and formic acids. The ions are therefore attracted to the $TiO_2$ surfaces, which have a net charge due to the photoelectric effect caused by the ultraviolet light impinging thereon. At the surface of the $TiO_2$ electrodes, the organic acids are juxtaposed to the OH radicals, and are readily oxidized. The presence of the catalyst thus substantially speeds the reaction, and also allows TOC measurement by oxidation of organics to $CO_2$, even in deoxygenated and deionized water streams.

According to a further aspect of the discoveries disclosed in the second continuation-in-part application, now U.S. Pat. No. 4,868,127, the reaction can be accelerated by electrophoresis. According to this technique, a voltage, typically 150 volts, is applied across the two electrodes in the sample chamber. When the deionized water sample enters the chamber, essentially no current flows. However, the ultraviolet rays falling on the water tend to break up organics in the water into relatively refractory but polarized ionic species, such as acetic acid and formic acid, as mentioned above. The electric field provided by the voltage across the electrodes then tends to accelerate the ions towards the electrodes, where they are conveniently and rapidly oxidized by OH radicals attached to the electrode surfaces. Electrolysis in combination with ultraviolet irradiation and $TiO_2$ catalysis is also a possibility, particularly in connection with relatively heavily polluted water streams and the like.

In a further aspect of the new discoveries disclosed in the second continuation-in-part application, now U.S. Pat. No. 4,868,127, the wavelength of the ultraviolet light is particularly critical in breaking up organics in the presence of a catalyst. In particular, the inventors have found that the 254 nm and 184 nm wavelength ultraviolet radiation emitted by particular low pressure mercury vapor lamps, in combination with a catalyst, is strikingly effective in breaking up relatively refractory organics. This discovery may have far-reaching implications in connection with the purification of water generally and is not limited strictly to instrumentation systems.

In the prior applications, mention was made of the fact that the surfaces of the electrodes were exposed to direct ultraviolet radiation. This was stated to be useful in keeping the electrodes clean and effective, by preventing growth of organics thereon. According to the discoveries described in the second continuation-in-part application, now U.S. Pat. No. 4,868,127, the direct exposure of the electrodes to UV is particularly significant because only in this case can the catalytic effect be obtained.

The present application reflects further refinements and improvements on the apparatus and methods disclosed and claimed in the parent applications. Specifically, this invention continues from the work disclosed in the "second continuation-in-part application" now U.S. Pat. No. 4,868,127, discussed above. Accordingly, the present application retains much of the text of that application and adds certain new material thereto.

In general, the methods and apparatus disclosed in the prior application were designed for TOC analysis of ultrapure or deionized water, that is, essentially water of very high conductivity. More specifically, the percentage of carbon dioxide resulting when the TOC in the water was oxidized by exposure to UV is a function of the conductivity of the water; depending on the conductivity of the water, a greater or lesser amount of the $CO_2$ is dissociated, i.e., is ionic. The remainder is dissolved as gas. Only the portion of the $CO_2$ which is ionic contributes to the conductivity of the water sample. In order that a simple conductivity measurement would be sufficient to accurately determine the amount of TOC initially present in the water, it was essential to limit the use of the instrument to deionized, highly resistive water samples.

According to an aspect of the present invention, by combining the TOC analysis instrument shown in the prior applications with a pH meter, accurate compensation can be made for some quantity of additional ions of known type in the water sample so that the instrument is useful with water of lower resistivity than otherwise. More specifically, as indicated, by restricting the instrument of the prior invention to a deionized water sample the resistivity of the water was uniformly very high, so that the relative solubility of the $CO_2$ would be substantially constant from sample to sample. This enabled an accurate determination of $CO_2$ content from a simple conductivity measurement. According to the present invention the pH of samples containing known additives such as chemical buffers is measured and used to determine the relative solubility of $CO_2$ in the water. Accordingly an accurate measurement of conductivity can be made with non-deionized waters.

Another improvement according to the present invention involves the method of analysis of the data used. Previously, the conductivity measurements made were corrected in accordance with variation in the sample temperature (typically occurring due to heating by the UV lamp) and the conductivity measurements were directly analyzed to detect completion of the oxidation reaction. As discussed above, the variation in conductivity of a water sample with $CO_2$ content is a non-linear function. Accordingly, it has now been recognized that an improvement can be made by temperature compensating the thermodynamic and electrochemical constants relating conductivity to $CO_2$ content, converting the conductivity values to values for $CO_2$ content using these corrected constants, and analyzing variation in the equivalent $CO_2$ values to detect completion of the reaction. By thus analyzing variation in equivalent $CO_2$ content, the nonlinearity of the $CO_2$ solubility/conductivity relation while the reaction is at or nearing completion can be eliminated from the analysis.

According to the present third continuation-in-part application there are also provided details of the currently preferred embodiment of the sample cell of the invention.

BRIEF DESCRIPTION OF THE DRAWINGS

The invention will be better understood if reference is made to the accompanying drawings in which.

DESCRIPTION OF THE PREFERRED EMBODIMENT

Figure 1:
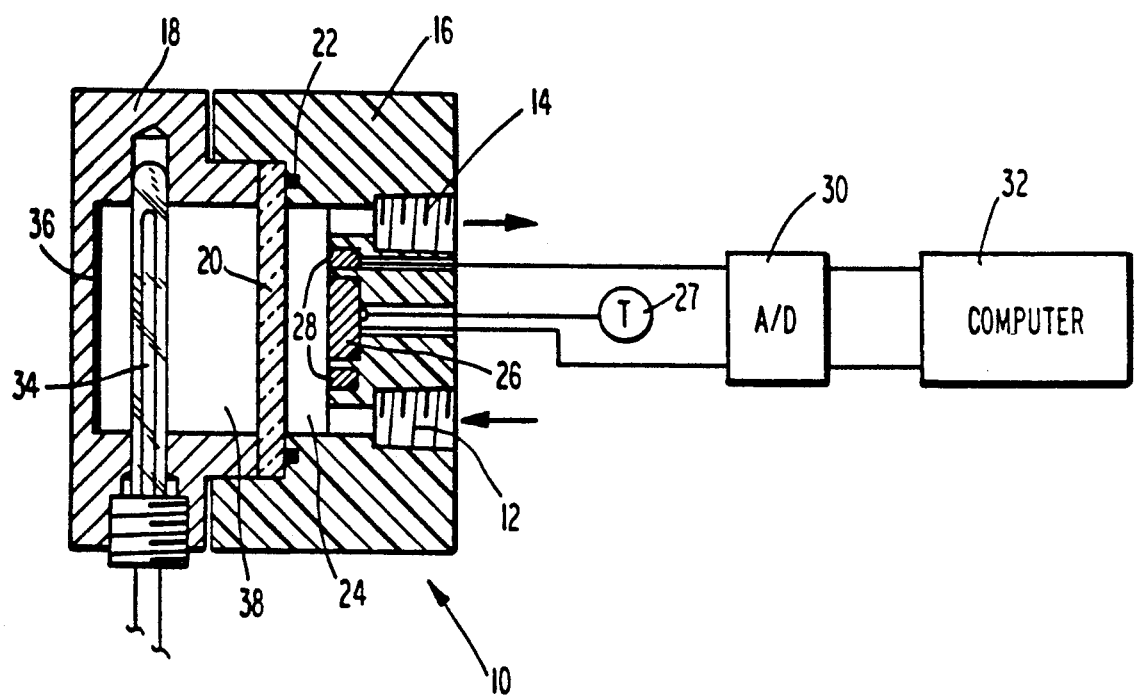
FIG. 1 is a cross-sectional view of the cell of the instrument according to the originally preferred embodiment of the invention and shows schematically its connection to other parts of the apparatus.

A typical sample cell according to the originally preferred embodiment of the invention is shown at 10 in FIG. 1. This cell is arranged to be connected at port 12 to a source of influent water, to be tested for the presence of organic carbon. The effluent water exits at port 14. Control valves (not shown) may be provided if necessary. In a high purity system, these may be of Teflon or similarly relatively inert materials. Typically, as noted, the process stream from which the water sample is taken may be deionized water from a semiconductor processing line, or pure water used in a nuclear power plant, or in pharmaceutical manufacturing, organic chemical research, bioengineering, and other high precision laboratory and industrial operations.

The cell 10 comprises two main body portions 16 and 18. Body portion 16 is preferably formed of Teflon, ensuring that a minimal quantity of impurities are leached out into the water stream. A recess in the Teflon body 16 is covered by a quartz window 20, quartz also being an inert material, thus defining the sample chamber 24. In cases of high pressure systems, it may be necessary to take steps to limit the pressure on the window 20. Fastening devices such as screws (not shown) connecting the two body portions 16 and 18 compress the quartz window 20 into an O-ring 22, ensuring a fluid-tight chamber 24. Within the fluid-tight chamber 24 are disposed two concentric circular electrodes 26 and 28, respectively, which may in a preferred embodiment, be made of titanium, or another electrode material chosen for resistance to diffusion; palladium, iridium, rhodium and platinum are some possible alternatives. In the preferred embodiment, the electrodes may be chamfered as shown, and are an interference fit within the Teflon body portion 16, ensuring a good seal therebetween.

The concentric electrode arrangement has several advantages. Chief among these is that the cell constant of this arrangement is quite high, ensuring relative sensitivity of the instrument to changes in conductance, whereas the capacitance between the two elements 26 and 28 is relatively low. As shown, the electrodes fit flush to the wall of the chamber; this discourages the formation of bubbles, fouling and the like. A conventional temperature sensor 27 can conveniently be attached to the rear of the central electrode 26 this is used to compensate for variation in sample conductance with temperature. The titanium electrodes are connected to a conventional analog/digital converter device 30 and then to a computer or similar data processing device 32 for monitoring changes in conductance of the water in the chamber 24 over time.

An ultraviolet lamp 34 is inserted through an orifice in the body portion 18, and this can be energized to supply ultraviolet light. The lamp 34 may be of the type known in the art as a low-pressure mercury vapor lamp. This class of lamp is chosen because its radiation is at primarily 253.7 nanometers wavelength with some 1-3% at 184 nanometers wavelength. Use of the 184 nanometer radiation, which is desired because light of this wavelength is very destructive to organic molecules, requires that the quartz window 20 be of a material which transmits this light well; a glass known as Supersil from Ameresil Co. works well. For similar reasons, the amount of water in the cell is deliberately kept small. The back of the chamber 38 is formed in the body 18 may be mirrored as indicated at 36 to ensure high efficiency use of the ultraviolet light. The chamber 38 within which the lamp is located is desirably filled with dry nitrogen or other non-absorbing gas. If it were filled with air or oxygen, for example, the oxygen would absorb some substantial fraction of the ultraviolet light emitted by the lamp 34.

Thus, in use, a sample of water from a process of interest is admitted to the chamber 24 and an initial background conductance reading is taken. The ultraviolet lamp is turned on, and the conductance of the water is monitored as a function of time by the computer 32. When the results of this monitoring indicate that the organic reaction has been completed, detected in a manner discussed in detail below, thus indicating that all the carbon in the organic matter has been converted to carbon dioxide, an output indicative of the total organic carbon content of the influent sample can be generated in accordance with the known relationship of carbon dioxide content in ultra-pure water to its conductance. See, e.g., "A New Approach to the Measurement of Organic Carbon," Poirier et al., *American Laboratory*, Dec. 1978, in which this relationship is shown.

The use of the sample chamber 24 as shown in FIG. 1 has several advantages. Probably the primary among these is that no movement of water or carbon dioxide between an irradiation chamber and a conductance measurement chamber is required, as in the prior art Regan patent, thus greatly lessening the opportunity for impurities and contaminants to leach out from the instrument and associated support system into contact with the sample which would be required if such an approach were employed. Furthermore, the direct exposure of the electrodes 26 and 28 to the UV light emitted by the lamp 34 serves to keep them free of organic contaminants and the like.

The net result is that generally the instrument itself is the only serious source of misleading ionic species in the water, "misleading" in the sense that it contributes spurious conductance not caused by oxidized carbon compounds. Accordingly, means must be found for compensation for these inaccuracies. This is particularly important in the case of low carbon level measurements, on the order of 100 ppb and less, because there the leaching of instrument materials such as the titanium of the electrodes is sufficiently rapid that the conductance does not stabilize as a function of time, i.e., the titanium continually leaches at a rate such that the conductance appears to continually rise. Similarly, even if the instrument is made of a relatively inert material such as Teflon, this material can make a spurious contribution. A similar effect, though of different sign, can occur due to absorption of the carbon dioxide by the Teflon. Other instrument contributions are doubtless possible.

In a manner subsequently described, the instrument system of the invention differentiates between all instrument contributions, which occur at a relatively constant rate during the oxidation of the organics, and the conductivity contribution of the carbon dioxide, at low-TOC concentrations. In such cases, the conductance value never stabilizes, because the instrument contribution continues. At higher organic concentrations, this is less of a problem, because there the instrument contributes relatively less to the total conductance of the water solution, and the conductance stabilizes to within experimental error to the asymptote of the conductivity curve due to oxidation of organics.

As mentioned according to the invention of the first continuation-in-part application (Ser. No. 635,551, now U.S. Pat. No. 4,666,860), the original cell design was substantially revamped to cope with certain problems and make certain improvements which were considered desirable. For example, it was found in experimentation with the original cell design that the Teflon material of the body of the cell had been absorbing and emitting carbon dioxide which would, of course, lead to inaccurate TOC measurement. Further, it appeared possible that the Teflon was degrading upon exposure to ultraviolet light. Hence, it was desired to eliminate all such materials and use only fused silica, titanium and Viton (trademark E.I. DuPont deNemours & Co.) in the cell construction. Further, it was deemed desirable to shield the Viton seals from direct UV radiation in case they should degrade if exposed to radiation.

Another object of the redesign of the cell was to lower its cell constant to approximately 0.1 in order to reduce electrical noise from the lamp.

Another difficulty with the initial cell design was that it did not have equal sensitivity throughout the sample. The new cell configuration was designed to ensure such equal sensitivity making the variation of conductivity over time more ideal and predictable.

It was considered desirable to design the cell to maintain its integrity up to 400 psi, matching common pulsed loads. This is particularly desirable because while it would be possible to lower the water pressure, depressurization will typically cause bubbles to form which will interfere with accurate measurement. Also, providing the sample cell with the capacity to handle 400 psi means it can be used in substantially all laboratory process streams simply by closing a valve on its output side to trap a sample of water for test.

Another object of the new cell design was to provide for easy lamp replacement, easy assembly of the chamber and to simplify the machining required.

Another object of the cell redesign was to ensure that the electrode configuration would integrate any variations in temperature throughout the cell sample, thus ensuring further uniformity of results. For similar reasons, it was desired that the temperature sensor, critical to ensure correct compensation of the conductivity results should be well isolated thermally from the environment while being in intimate contact with the solution, and that the bulk of the titanium metal, which forms the electrodes, should be isolated thermally from the environment so that the electrodes can quickly reach thermal equilibrium with the sample. Similarly, so that the temperature variation can be limited as much as possible, the amplifier used to amplify the signal should be thermally isolated from the chamber so that amplifier-generated heating is not transmitted to the sample.

Finally, it was desired to redesign the chamber such that it is flushed quickly and thoroughly when a sample has been completely oxidized, so as to provide short purge time requirements, and to minimize any possibility of bubble entrapment or residual contamination.

Additional design goals which would be desirable though not as critical as those just discussed include making possible the addition of positive temperature control devices. For example, a thermoelectric cooler might be affixed to the sample housing and used in a feedback loop to control sample temperature, eliminating temperature compensation of conductivity as an essential part of the TOC determination.

Finally, it was desirable to design the chamber to allow viewing of the sample chamber in situ, e.g. to determine that no foreign matter is present or the like.

Figure 11:
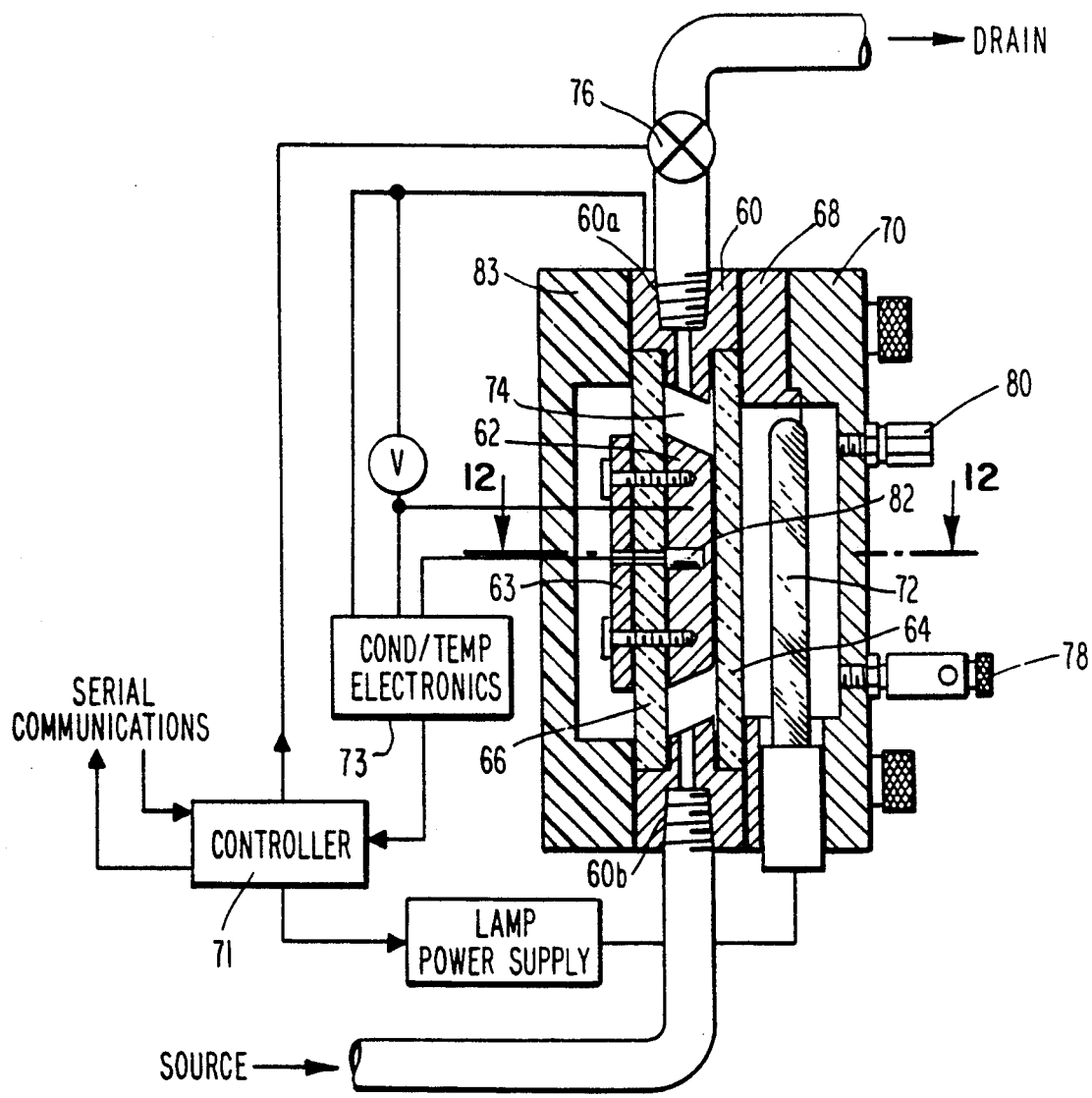
FIG. 11 is a cross-sectional view of the later-preferred embodiment of the invention.
Figure 12:
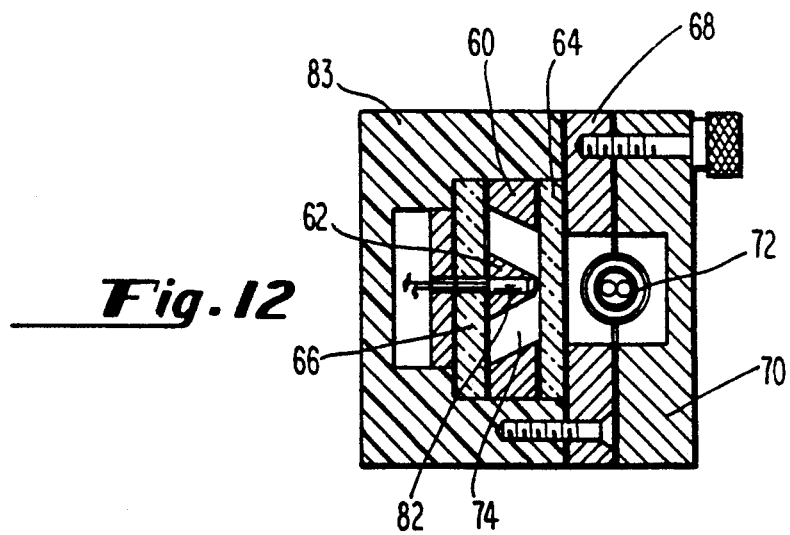
FIG. 12 is a cross-section taken on the line 12—12 of FIG. 11.

FIGS. 11 and 12 show the preferred embodiment of the cell of the invention as of Dec. 5, 1986, that is the filing date of Ser. No. 938,634, from which the present application depends. FIG. 11 additionally shows its connections to the remainder of the system. FIG. 12 is a cross-sectional view taken along the line 12—12 of FIG. 11. Broadly, the water sample is admitted to a sample chamber defined by an outer electrode 60, an inner electrode 62 and glass windows 64 and 66. The outer electrode 60 is formed with an inlet port 60b and an outlet port 60a as shown. The inlet is plumbed directly to the pressurized ultrapure water source and the outlet is fed to a drain. A sample valve 76 is interposed in the outlet line. Under control of controller 71, the measurement cycle starts by closing the valve 76, halting the purge flow and trapping a sample of water to be analyzed. The background temperature-corrected conductivity between electrodes 60 and 62 is measured by electronics unit 73. An ultraviolet lamp 72 is turned on and oxidizes the organic material present in the sample. The resultant temperature-corrected change in conductivity is measured, the $CO_2$ concentration calculated therefrom and the organic concentration displayed as parts per billion total organic carbon on a display on controller 71. The valve 76 is then opened, allowing a new supply of water to purge the chamber and clean it for the next cycle.

The sample chamber is constructed entirely of titanium and high-purity synthetic fused silica such as that referred to as Supersil, mentioned above. The seals required to contain the sample are formed of a durable material such as Viton, and are shaded from direct ultraviolet exposure, in order to avoid degradation and consequent interference with the measurement. Preferably, the sample chamber is vertically oriented with the outlet on top to allow easy flushing of bubbles. The chamber is designed to operate at system pressure with a continuous pressure rating of 150 psi and a pulse rating of 400 psi. Because the sample valve 76 is a potentially severe source of contamination in low concentration TOC measurement, it has been located downstream from the sample, eliminating these problems.

As discussed earlier, use of 184 nanometer radiation is highly desirable because this breaks up molecular oxygen to provide radicals for combination with the carbon, and is a very powerful oxidant. However, the low-pressure mercury vapor lamp used outputs only some 1-3% 184 nm UV. The remainder is primarily 254 nanometer UV radiation. Accordingly, it is important that the glass selected transmit both frequencies very well, and the Supersil material mentioned above does so. It will be recognized by those skilled in the art that the absorptivity of the 184 nanometer radiation by oxygen means that it would be undesirable to have the lamp 72 surrounded by air. A fill valve 78 and a check valve 80 are provided for filling a sealed chamber enclosing the lamp 72 with nitrogen. Ordinarily, of course, this chamber would be filled with nitrogen at the factory. In the event lamp replacement is required, this allows simple purging by the user.

As will be appreciated from the view of FIG. 11, the conductivity sensor is in fact integral to the sample chamber. The opposing electrodes 60 and 62 are equidistant to produce equal volume sensitivity throughout and are spaced to provide a cell constant just over 0.1. The surfaces of the electrodes are constantly exposed to intense short wave ultraviolet radiation which keeps them clean and free of organic contaminants which would interfere with high accuracy conductivity measurements. Contained within the center electrode 62 is a solid-state temperature sensor 82, typically a Model AD 590LF from the Analog Devices Company. Thermistors could also be used. This sensor is capable of temperature measurement accuracy of $\pm 0.05°$ C. The large surface area and large electrode volumes serve to integrate the sample temperature over the entire chamber, thereby providing an accurate representation of the mean temperature of the sample. The center electrode 62 is clamped to the glass window 66 by way of a backplate 63, which confines the temperature sensor 82 by position. The cell assembly is completed by a transparent plastic rear cover 83. Through it one can observe the UV light from the lamp passing through both the first and second windows 64 and 66, around the inner electrode. The leads to the temperature sensor 82 and the center electrode 62 pass through a hole in the rear cover 83, while electrical connection to the outer electrode can be made directly thereto. It will be observed that the lamp 72 is clamped between members 68 and 70, formed of aluminum, and can be removed without breaking the seals of the sample chamber, enabling inspection of the chamber in situ.

Figure 13:
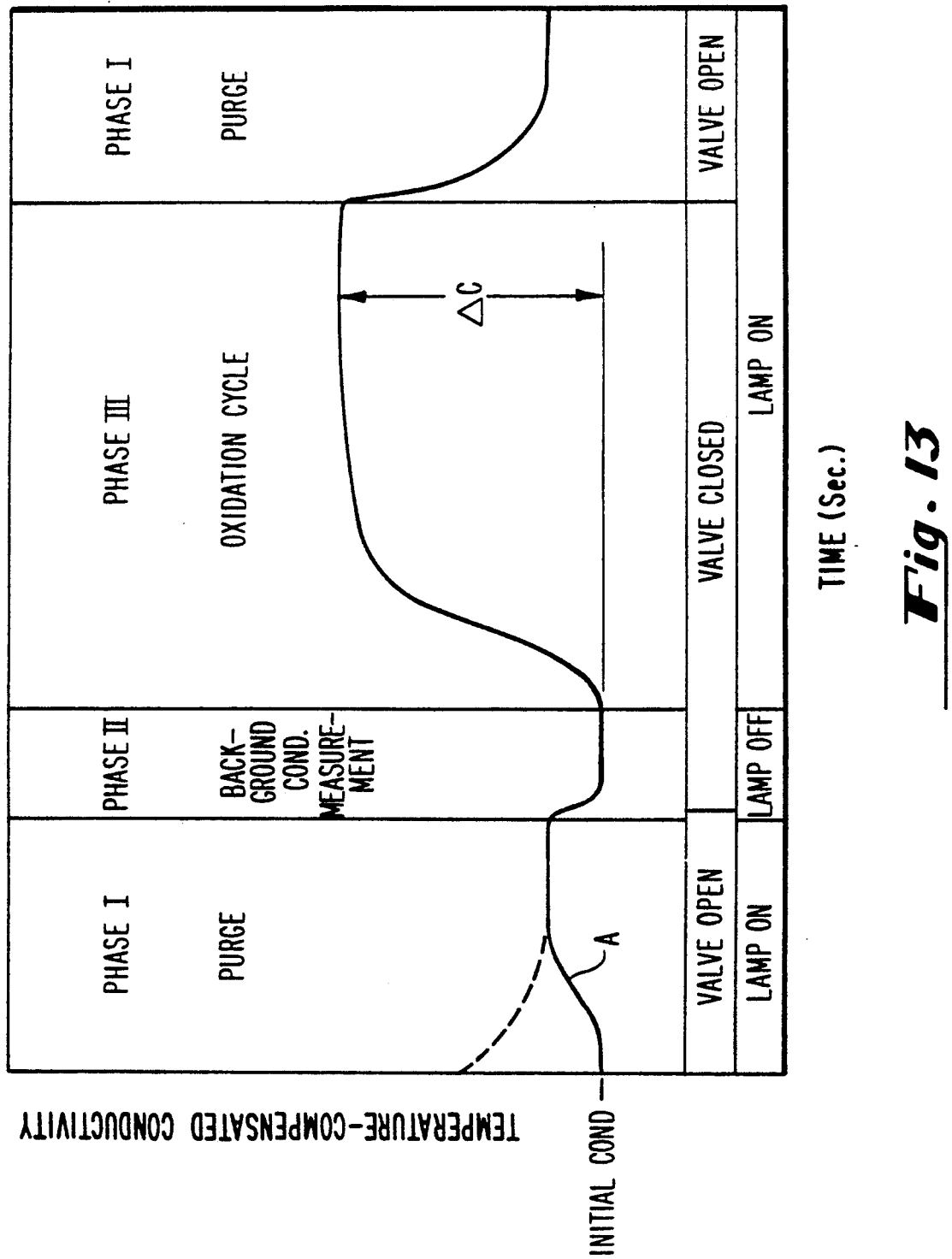
FIG. 13 is a timing chart, with a plot of typical conductivity data.

FIG. 13 shows the sequence of operation of the instrument according to the invention. The graphed data shown at A represents conductivity measured as a function of time. The two bar graphs along the bottom of FIG. 13 show the sequence of opening and closing of the valve 76 and the periods during which the lamp 72 is illuminated. Thus, in phase I the valve is opened and the lamp 72 is turned on. During this period, water from the source is passed through the sample chamber continuously, providing a purge effect.

The light is on to oxidize any material which may remain in the chamber. The lamp is turned off leaving the valve open for a short time to allow purging of any residual $CO_2$. The valve is then closed for Phase II, during which the background conductivity, that is, the conductivity of the sample before oxidation, is measured. The valve stays closed in Phase III but the lamp is turned on. During this time, the oxidation of organics to $CO_2$ causes the conductivity to gradually rise, typically to an asymptotic value as shown, which behavior is discussed more fully hereafter. The difference $\Delta C$ between the initial and final conductivity is shown. When properly temperature compensated, $\Delta C$ provides an indication of the total organic carbon content of the initial water sample. Phase I then begins again, as shown at the right side of FIG. 13.

The following discussion of FIGS. 2 through 10 appeared in substantially identical form in the original application and remains here because the analysis provided is applicable in many cases. Following this discussion, additional material explaining new understanding of the oxidation process and referring to FIGS. 14-17 will be provided.

Figure 2:
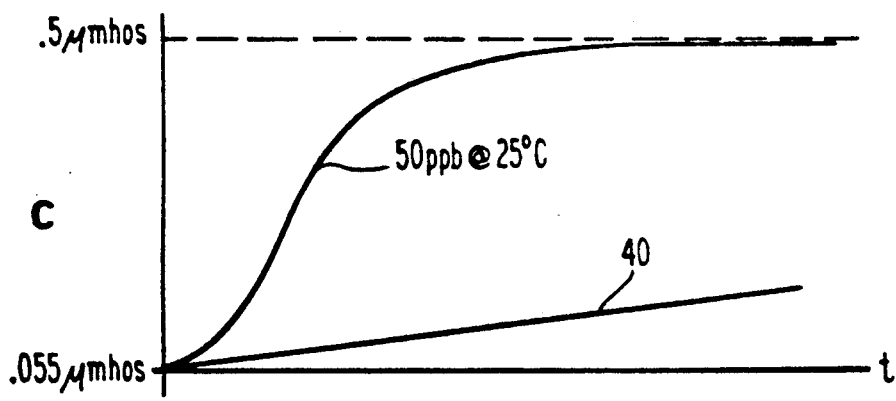
FIGS. 2 through 9 show various curves useful in understanding the operation of the system of the invention.

FIG. 2 shows an idealized plot of the conductivity of water, corrected for temperature and instrument background variations, the organic carbon content of which is being oxidized by ultraviolet light, versus time. Here the vertical axis is conductivity C; the conductivity C can vary from the conductivity of pure water, 0.055 micromhos at 25° C. at the origin, to on the order of 0.5 micromhos for 50 ppb organic-carbon contaminated water, through perhaps 5 micromhos at water contaminated at 5 ppm, both again at 25° C. It will be observed that the exemplary curve shown approaches an asymptotic limit, which is usual. Typically, this limit will be approached in on the order of one to five minutes after commencement of exposure of the water to ultraviolet light. It will also be observed that the curve is substantially non-linear.

Figure 3:
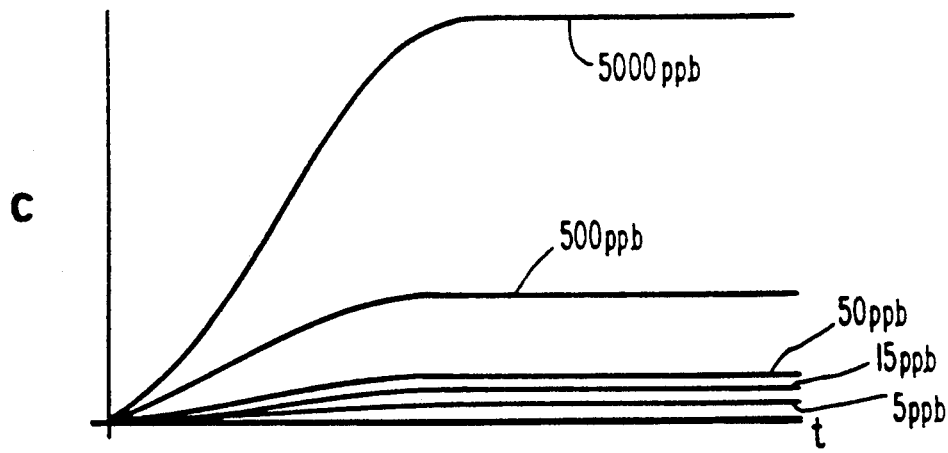

FIG. 3 shows a number of additional curves of the conductivity of water samples containing various amounts of organic carbon, as noted, being oxidized as a result of exposure to ultraviolet radiation as a function of time. It will be observed that the relative differences between the asymptotic portions of the curves for widely varying concentrations of contaminants are not very great, particularly in the low-TOC region. That is, the ultimate conductivity of water samples after oxidation of relatively widely varying amounts of organic materials are quite similar. Accordingly, if these samples are to be distinguished from one another by measurement of conductivity, any background noise or other spurious contribution must be rigorously eliminated, and the present invention is designed to achieve this goal.

Figure 4:
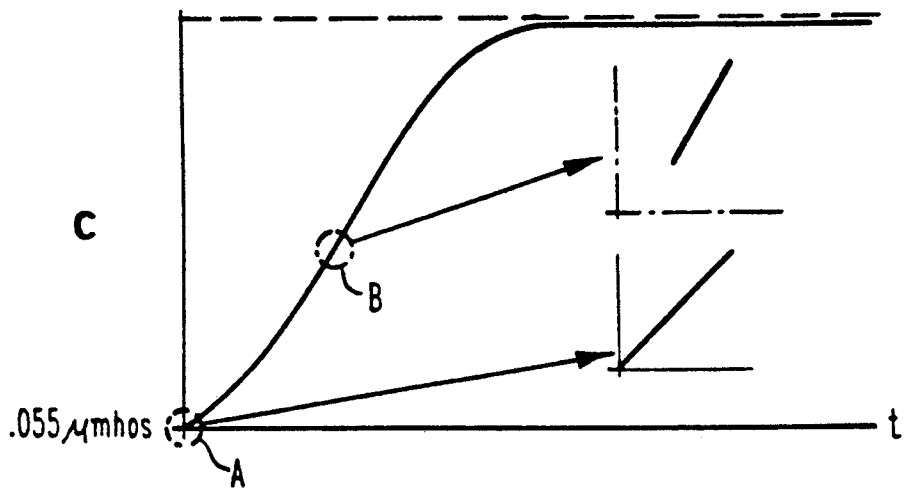

FIG. 4 shows a curve depicting the variation of the temperature-corrected conductivity of organic-free water sealed in the sample chamber and irradiated with ultraviolet light as a function of time. The variation is due to leaching of titanium into the water, or other instrument contribution. In this figure the time scale is on the order of several days. It will be observed that this curve also approaches an asymptotic limit as the water becomes saturated by the instrument contribution but that the portion of the curve of interest, that within a circle A of a few minutes' radius around the origin, as shown enlarged on the right side of FIG. 4, is relatively linear. As indicated at B, other small portions of the total curve are also substantially linear. Again, the origin is at 0.055 micromhos, the conductivity of pure water, and the conductivity can rise to a very high value in the case of saturated water. However, the time required for approaching the saturation point is on the order of days.

If one expands the very left most portion of the curve of FIG. 4, indicating variation of conductivity due to the instrument contribution and inserts this at 40 into FIG. 2, showing variation in conductivity due to oxidation of organic material to carbon dioxide, and sums the two curves, thus providing a curve indicative of the typical shape of real data detected in measurements made according to the invention, the horizontal portion of the curve of FIG. 2 will be replaced instead with a linear portion superimposed upon the non-linear portion of the curve of FIG. 2, and this behavior is frequently observed.

Figure 5:
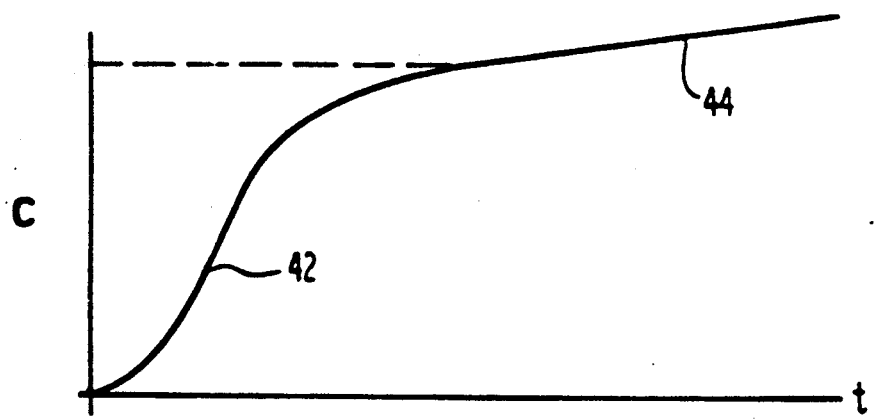

FIG. 5 shows an example of typical test data of this kind. The non-linear portion 42 of the curve is similar to that of FIG. 2, whereas the linear but non-horizontal portion 44 is the result of the addition of the linear portion of curve 40 of FIG. 2 due to instrument background.

Figure 6:
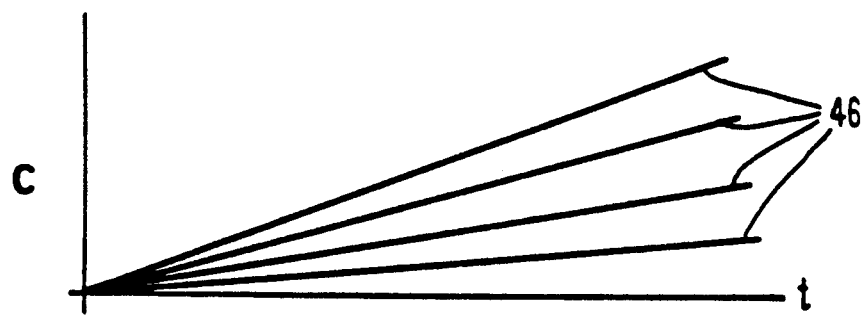

It might be considered, therefore, to be a simple matter to measure the curve of saturation of a typical instrument design, curve 40 of FIG. 2, e.g., at initial manufacture of the instrument, and subtract this from actual test data so as to yield a compensated curve. However, in fact this does not yield accurate results. FIG. 6 shows one reason why. The several curves 46 shown there all correspond to the curve 40 in FIG. 2. These curves indicate that while the instrument contribution may be relatively linear for the several minutes during which a given TOC measurement is made, this rate is not the same for all samples and under all circumstances, so that these measurements are not repeatable. This prevents a base line measurement from being established for correcting test data as suggested Furthermore, it appears likely to the inventors that exposure of the instrument material to ultraviolet light may also increase its contribution in a not entirely predictable fashion, such that this effect would similarly lead to inaccuracies if simple subtraction of a baseline correction were made to actual experimental data. Accordingly, more sophisticated techniques for determining when the organic carbon oxidation reaction is complete and for calculating the correction to be applied are required, and these are provided by the invention as well.

Figure 7:
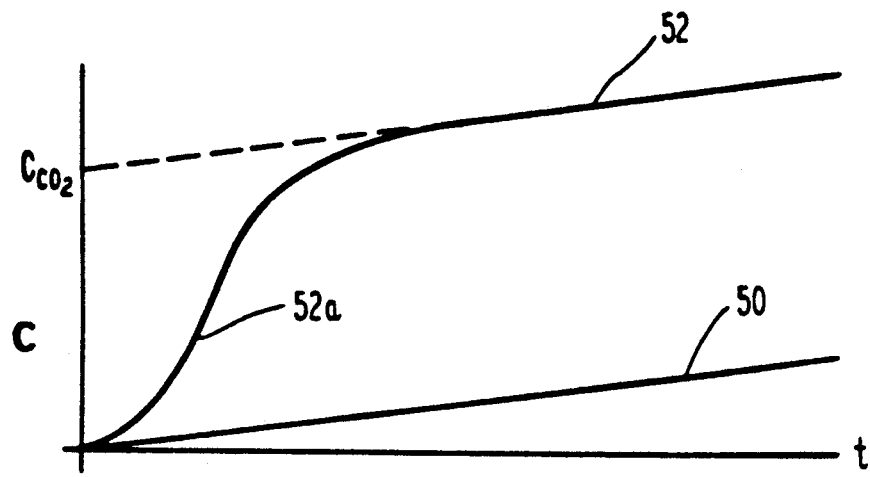

FIG. 7 shows an enlarged view of a curve comparable to that shown in FIG. 5, illustrating the differentiation between the instrument conductivity contribution versus time curve 50, which is substantially linear for the short time (e.g., 1-10 minutes) shown and the curve 52, which plots measured conductivity versus time data. The non-linear portion 52a of curve 52 is that due to oxidation of carbon components to form carbon dioxide. Once this reaction is essentially complete, curve 52 also becomes linear. The subsequent increase in temperature-corrected conductivity is due solely to the instrument contribution. Therefore, the linear portion of curve 52 can be extended leftward to the conductivity axis, where the intercept $C_{co2}$ provides a measure of the difference in conductivity between the total curve 52 and the portion 50 contributed by the instrument, i.e., a measure of the portion contributed solely by the carbon dioxide resulting from oxidation of organic carbon. This value for conductivity $C_{co2}$ can then be directly converted to a value for total organic carbon in the sample, e.g., using the data shown in the article by Poirier et al referred to above.

Figure 8:
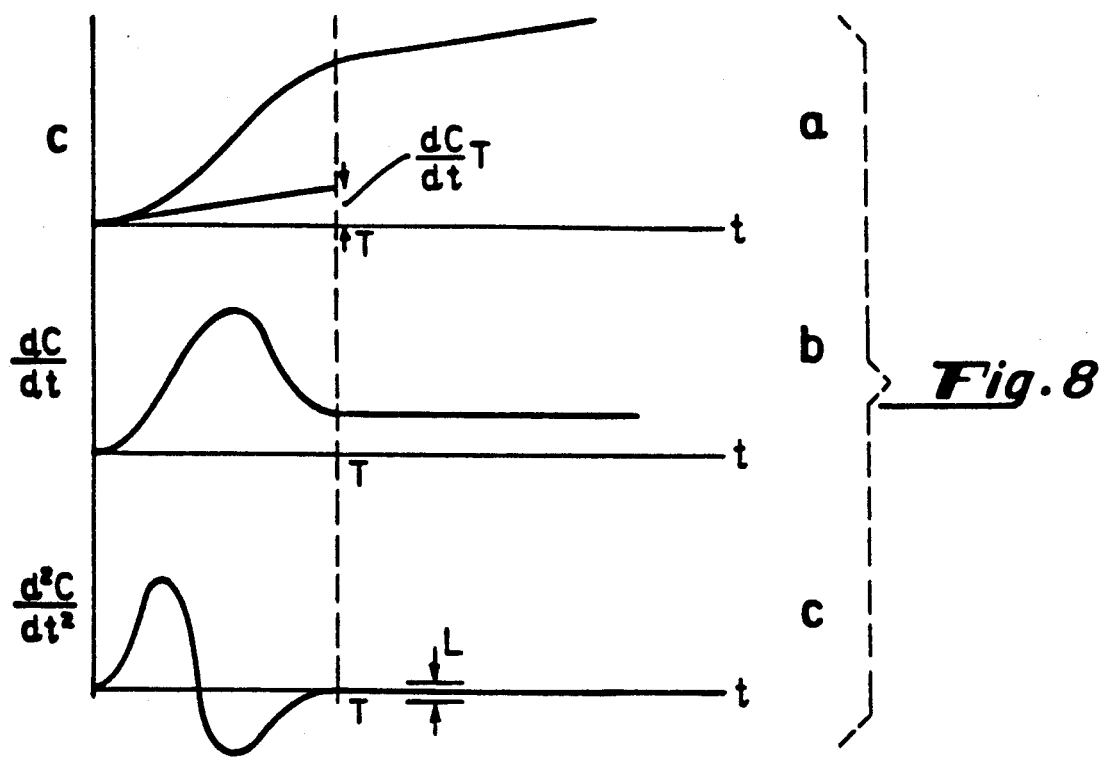

The sole difficulty with the approach just outlined is that it is not necessarily easy to determine by computer when the curve 52 has become linear. FIG. 8 shows three curves, denoted FIGS. 8a through c, which illustrate a way in which this determination can be made. FIG. 8a is a reproduction of curve 52 of FIG. 7, showing the characteristic non-linear/linear shape of the conductance versus time curve. FIG. 8b shows the time derivative of this curve, denominated dC/dt on the vertical axis, versus time. It will be observed that the first derivative essentially reaches a horizontal but non-zero value when the reaction is completely, indicated by the dashed line at time T. FIG. 8c shows the second time derivative of conductivity plotted versus time, $d^2C/dt^2$. When the value of the second derivative settles to within some small specified value L of zero, designed to account for sampling errors and the like, the conductivity curve of FIG. 8a has become linear, indicating that oxidation is complete. Assuming all values are appropriately temperature-compensated, one can then generate a value for the correction to be applied simply by subtracting the contribution given by the instrument, (dC/dt) T, that is, the slope of the instrument contribution curve, dC/dt, times T, the time at which oxidation is determined to be complete, from ΔC, the total change in conductivity at time T. The remainder is equal to the conductivity contribution of the carbon dioxide; as mentioned above, this value can be directly converted to a value for total organic carbon in the water sample prior to oxidation by the UV light.

Figure 9:
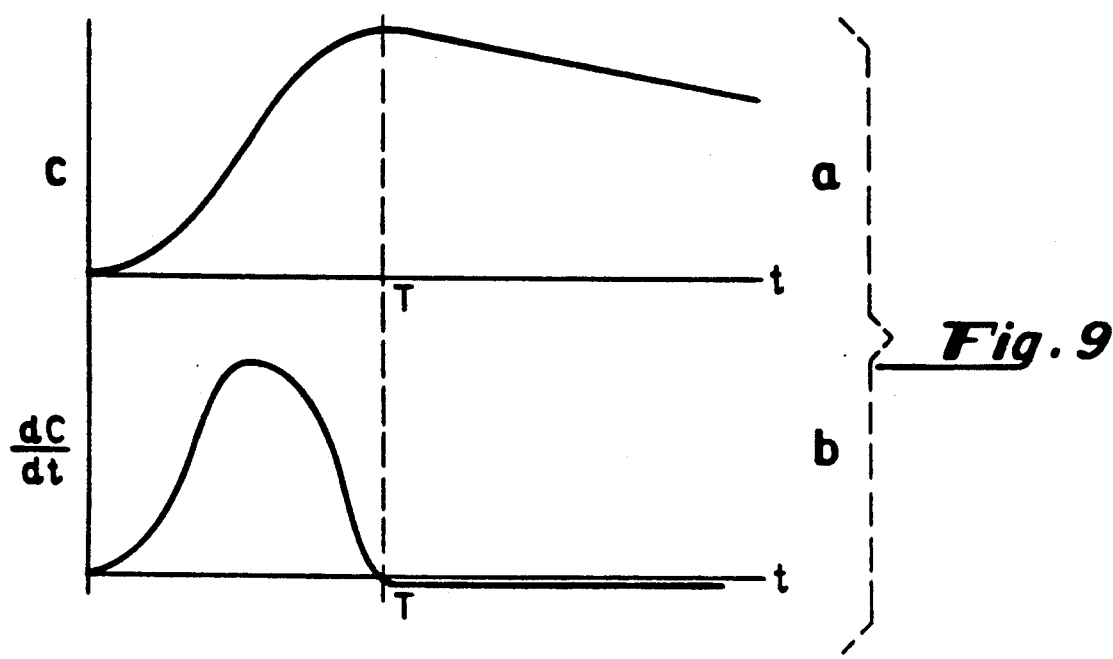
Figure 10:
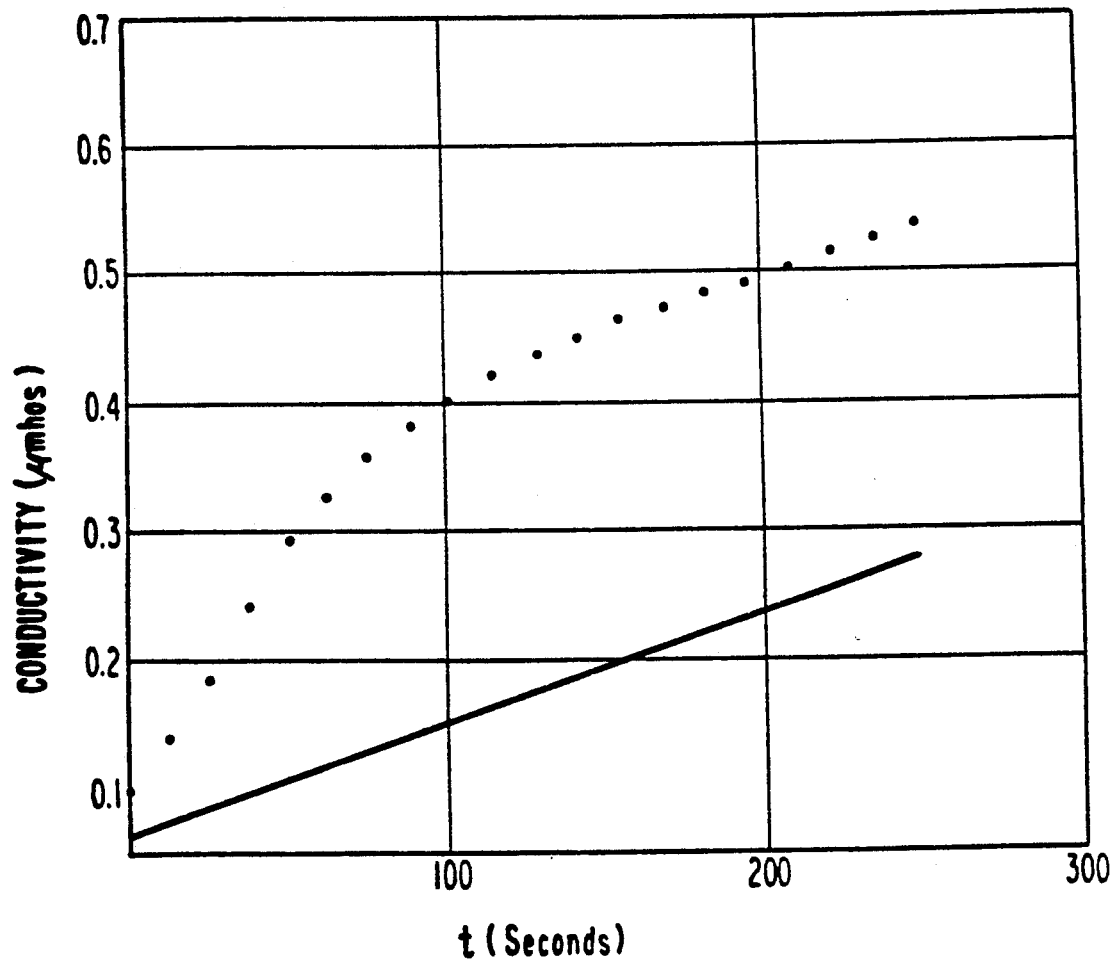
FIG. 10 shows an example of actual test data.

The situation just described and the curves shown in FIG. 8 occur where the contribution to the conductivity of the water of total organic carbon is relatively low compared to that caused by the instrument. In such situations, completion of oxidation can be detected responsive to approach of the second derivative to zero. In other cases, where the total organic carbon content is relatively high, or when the instrument is first installed, differing techniques are indicated. FIG. 9 shows such a situation, in which the conductivity of the water, shown in FIG. 9a, reaches a peak and then begins to decline. This occurs, for example, because the carbon dioxide diffuses through the water lines connected to the sample cell, reducing the conductivity of the water. It is clear, however, that once the conductivity has peaked and begun to decline, the reaction has been completed. Accordingly, the conductivity data at this point indicates the total organic carbon content of the sample. This value can be noted readily by monitoring the time derivative of this curve, shown in FIG. 9b. When the derivative reaches zero or becomes negative, as shown, the reaction has been completed, and the conductivity at this time indicates that the amount of total organic carbon being oxidized to carbon dioxide can be calculated. Here, the contribution from the instrument is minor and can be ignored.

The inventors find that with a sample cell substantially as shown, if one simply monitors both first and second time derivatives, either the first derivative or the second derivative will approach zero, as in FIGS. 9 and 8, respectively, depending on the total organic content. The FIG. 8 curve is usually seen at TOC values less than 50 ppb, while the FIG. 9 curve becomes typical at higher TOC concentrations, the threshold being a function of actual instrument background contribution.

Those skilled in the art will recognize that there are several ways in which the first and second time derivatives as described in FIGS. 8 and 9 can be calculated nique used, and because the first derivative is used in calculation of the second derivative. The conductivity measurements shown are graphed in the upper curve of FIG. 10. As can be observed, the curve is linear at its rightmost extremity indicating that the oxidation reaction is complete, and that further changes in conductivity are due to instrument contribution at the linear rate shown by the lower curve.

EXAMPLE I

| Time (HR:MIN:SEC) | Elapsed Time (SEC) | Conductivity (MICROS) | Temp. (°C.) | DC/DT (MICROS)/SEC | D2C/DT2 (MICROS)/SEC2 |
|---|---|---|---|---|---|
| BACKGROUND MEASUREMENT | | | | | |
| 9:38:35 | 0 | .065 | 23.81 | 0 | 0 |
| LAMP ON, OXIDATION BEGINS | | | | | |
| 9:38:50 | 0 | .099 | 24.02 | 0 | 0 |
| 9:39:3 | 13 | .139 | 24.16 | 0 | 0 |
| 9:39:16 | 26 | .185 | 24.32 | 0 | 0 |
| 9:39:28 | 38 | .243 | 24.49 | 0 | 0 |
| 9:39:41 | 51 | .293 | 24.67 | 3.8874803E-03 | 0 |
| 9:39:54 | 64 | .326 | 24.86 | 3.8090918E-03 | 0 |
| 9:40:6 | 76 | .357 | 25.05 | 3.3872851E-03 | 0 |
| 9:40:19 | 89 | .381 | 25.25 | 2.6544229E-03 | 0 |
| 9:40:32 | 102 | .401 | 25.42 | 2.1485315E-03 | −3.5957636E-05 |
| 9:40:45 | 115 | .42 | 25.57 | 1.8229599E-03 | −4.0926163E-05 |
| 9:40:59 | 129 | .436 | 25.73 | 1.4988779E-03 | −3.526866E-05 |
| 9:41:12 | 142 | .448 | 25.9 | 1.278984E-03 | −2.5812067E-05 |
| 9:41:25 | 155 | .462 | 26.08 | 1.1222675E-03 | −1.9353856E-05 |
| 9:41:39 | 169 | .47 | 26.21 | 9.398618E-04 | −1.6001923E-05 |
| 9:41:52 | 182 | .483 | 26.32 | 8.734737E-04 | −1.2081323E-05 |
| 9:42:6 | 196 | .491 | 26.47 | 7.912241E-04 | −9.05495E-06 |
| 9:42:19 | 209 | .502 | 26.58 | 7.4734534E-04 | −6.680404E-06 |
| 9:42:32 | 222 | .514 | 26.68 | 8.0459425E-04 | −2.872771E-06 |
| 9:42:46 | 236 | .525 | 26.83 | 7.978849E-04 | −1.039593E-06 |
| 9:42:59 | 249 | .534 | 26.96 | 8.219301E-04 | 8.10708E-07 |
| OXIDATION COMPLETE | | | | | | and evaluated. It is envisioned that in the ultimate embodiment, dedicated analog differentiation devices could be used. Possibly these could be integrated with other circuit elements designed to indicate the total organic carbon directly. In the meantime, it will be sufficient teaching to those skilled in the art to note that a general purpose digital computer together with a conventional analog-to-digital converter device for conversion of conductivity data into digital values can be used.

In a preferred embodiment which has been successfully tested, the conductivity is measured every 13 seconds, and the last 5 data points thus generated are successively curve-fit to a straight line the slope of which is monitored to determine whether the first derivative has approached the horizontal. The second derivative is generated similarly by curve-fitting five successive first derivative values to a straight line the slope of which is similarly measured. Whichever derivative first approximates zero is then used as described above in derivation of the conductivity contributed by oxidation of total organic carbon. The approach selected is thus dependent on the relative amount of total organic carbon as compared with the rate at which the instrument contributes to the conductivity of the water sample.

The following Example I is a reproduction of the output of an actual run in which the total organic content of a water sample was measured as described above. The six columns of data represent, reading left to right, sampling time, elapsed time, conductivity in micromhos, sample temperature in °C (measured at the rear of the center electrode) and the first and second time derivatives of the conductivity measurements. The last two items mentioned do not begin until the fifth and ninth entries, due to the five-sample curve-fitting technique used, and because the first derivative is used in calculation of the second derivative.

Elapsed Time (Oxidation)—4 minutes, 9 seconds
Initial Background Conductivity=0.65 micromhos/cm
Final Background Conductivity=0.279857 micromhos/cm
Temperature Change=3.15° C.
Delta Conductivity (Instrument)=0.20466059 micromhos/cm
Delta Conductivity ($CO_2$)=0.254143 micromhos/cm
TOC=10.341327 PPB
Uncorrected TOC=33.676432 PPB The computer output reproduced above indicates that the oxidation reaction proceeded to completion in some 4 minutes, 9 seconds, that the initial background conductivity of the water was 0.065 micromhos/cm, that it rose due to instrument contribution to a final value of 0.279 micromhos/cm and that the temperature change (used by the computer to correct the conductivity values so as to be comparable to one another) was 3.15° C. The value for L used was $\pm 10^{-5}$; after five successive values of the second derivative of the conductivity value were less than L, the change in conductivity due to the instrument was calculated to be some 0.204 micromhos/cm. and that due to oxidation of carbon was 0.254/micromhos/cm. From this last figure an initial total organic content of the water sample of some 10.3 parts per billion was calculated; if the correction for the instrument contribution had not been applied, the apparent TOC value would have been 33.6 ppb. The method of the invention of correction for this source of spurious conductivity is thus clearly beneficial.

It will be recalled from the discussion of FIGS. 8 and 9 that essentially two cases of conductivity variation with time upon exposure of a water sample containing organic matter to ultraviolet light were discussed. FIG. 9 discussed the case in which the conductivity value either reached a constant or went into a steady decline after a period of time. This will be referred to hereinafter as a Case I contaminant. Note that the loss of $CO_2$ causing a steady decline in the measured conductivity with time can be substantially eliminated by proper instrument design. FIG. 8 displayed the case in which the conductivity varied nonlinearly for a period of time and then reached a linear gradually increasing condition. This will be referred to hereinafter as Case II condition. It has since been discovered that there is a third type of contaminant which reaches an intermediate peak and then declines to a steady value. This will be referred hereinafter as a Case III contaminant. Case III behavior is believed to be encountered when the contaminant is oxidized through intermediate products which are of higher conductivity than the final $CO_2$ product. Acetone provides a good example of this behavior. Another common chemical which is oxidized through intermediates is butanol.

Figure 14A:
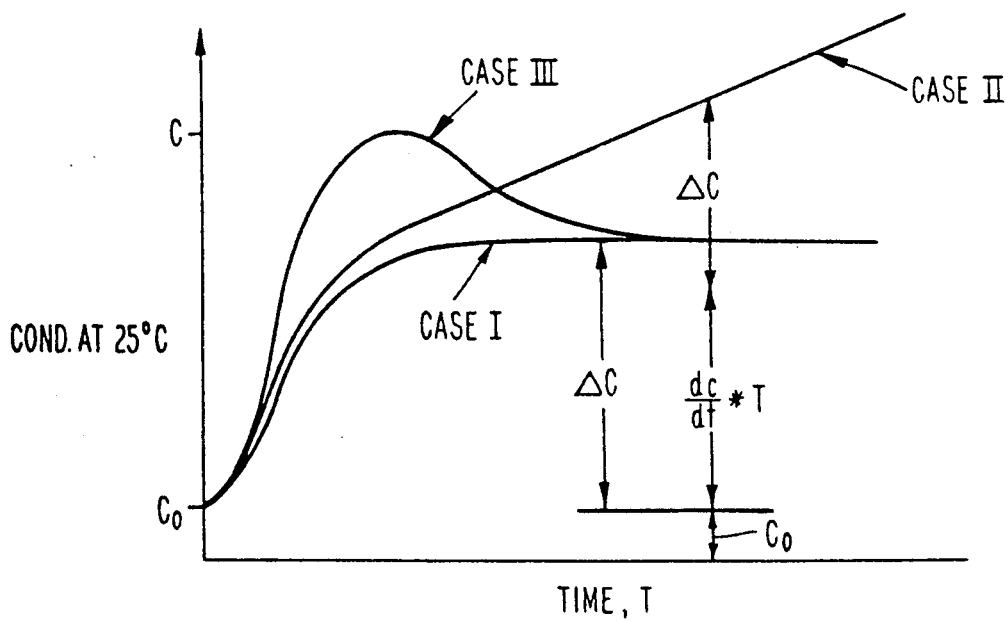
FIGS. 14A-14C are graphs of idealized conductivity data, and the first and second time derivatives thereof.
Figure 14B:
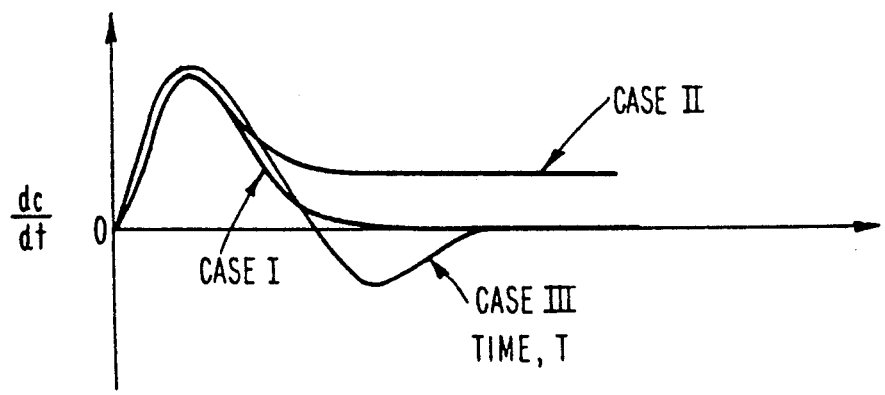
Figure 14C:
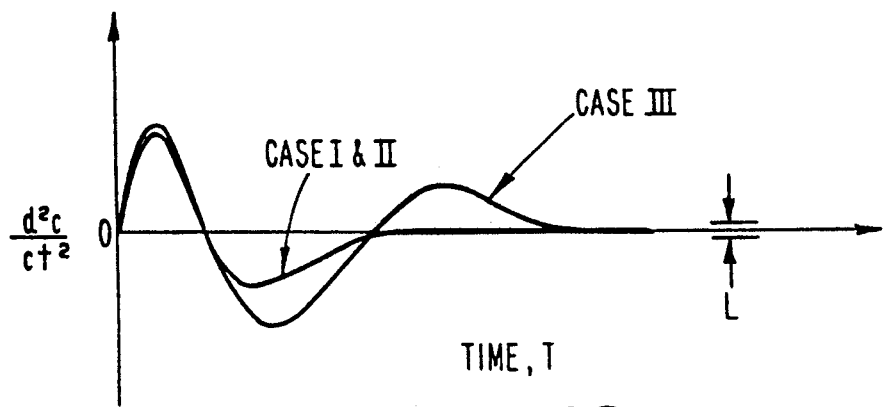

A comparison of idealized examples of Case I, II and III behavior is shown in FIG. 14. FIG. 14(a) shows conductivity as a function of time, for Cases I, II and III. FIG. 14(b) shows the first time derivatives of the conductivity curves versus time, and FIG. 14(c) show the second time derivatives of the conductivity curves again versus time. As shown and described above, the Case I behavior corresponds generally to that shown in FIG. 9, ending at a linear asymptote (either horizontal or dropping) while the Case II behavior (a rising asymptotic limit) is that shown in FIG. 8. The Case III data as shown in FIG. 14(a) exhibits conductivity reaching a peak at some early value and then declining to a final asymptotic value after the oxidation reaction is complete. It is a relatively straightforward matter to determine when a Case III contaminant has been completely oxidized, i.e. when its conductivity becomes a constant, by monitoring the first and second derivatives as discussed above in connection with Case I and II behavior. A further improvement can be made by noting that the point at which the second time derivative of the Case III conductivity, FIG. 14(c), passes through zero for the second time, is the inflection point of the conductivity versus time plot of FIG. 14(a) and that in neither Case I nor Case II does the second derivative pass through zero twice. Accordingly, when the second time derivative passes through zero a second time, it can be concluded that the sample includes a Case III contaminant. When the first time derivative thereafter approaches zero, the conductivity is reaching its asymptotic limit. At this time compensation can be made for the background conductivity of the sample, $C_o$ in FIG. 14(a), which is then subtracted from the total change in conductivity, $\Delta C$. The remainder is then temperature-corrected to yield an accurate conductivity value which can then be converted to a TOC value as discussed above.

Accordingly, analysis of the Case III data is accomplished by a refinement of the techniques used in connection with data from Cases I and II. The second derivative is monitored to determine whether it goes negative, then passes through zero again. If the first derivative is negative when the second derivative curve reaches zero for the second time, a Case III curve is in progress, and the reaction has proceeded to the inflection point of the corresponding conductivity curve. Two different tests can now be applied to determine whether a Case III curve has approached its asymptotic limit: either the first derivative can be monitored to determine when it is at an acceptably low level, or the second derivative of the conductivity can be monitored until it again approaches zero from the positive side.

Data shown hereinafter indicates that in many cases Case III reactions are not completed for a relatively long period of time, typically 15 or 20 minutes. Known first order chemical kinetics accurately describe the reaction rate at the low concentrations of contaminants in the solutions analyzed by the instrument of the invention. In such cases the variation in conductivity is described with respect to time by an exponential equation. Accordingly, as the reaction approaches completion, the last portion of the exponential curve approaches an asymptotic limit. It is possible to curve fit an exponential or similarly-shaped curve to this portion of the data and calculate the final conductivity value from the asymptote. Furthermore, when analyzing a series of samples from stable systems, the peak value reached by the conductivity of any particular sample is as repeatable as the final conductivity of the sample. Accordingly, if one monitors a series of peak conductivity values obtained from samples from the same laboratory equipment, process plant, testing station or the like, and finds that the peak values reached by the conductivity are all within a predetermined limit, e.g. ±2%, of one another, one can conclude that the final conductivity value will similarly be within ±2% of that of a run continued for the full period, and can presume that accordingly there has been no significant change in the organic concentration of the water sample tested. This is very useful in continuous monitoring of a given process, and can readily be adapted to trend detection and display. In practice, the controller 71 operating the system monitors conductivity of a succession of samples, dumping them immediately after reading the peak value, except when the peak value departs by more than a predetermined value from one or more previous peak values.

The following Example II gives an indication of the data which is generated during an extended analysis of a sample containing a Type III organic contaminant. As can be seen, the example is generally comparable to that shown above as Example I, though additional data columns are presented. It should be emphasized that the data given for the first and second time derivatives necessarily do not show values corresponding to the first few conductivity values, due to the nature of the process used to derive these functions, which is as discussed above. It will be observed that after the run had proceeded for 208 seconds, it was made clear that a Case III contaminant was present. This was determined by noting that the first derivative had become negative. When the second derivative of the conductivity became positive after 317 seconds (for the second time, in fact, although the first positive values do not appear in Example II), the peak value of the conductivity was compared to an earlier run and it was determined that the deviation was some 0.843%. This was greater than the deviation allowance of 0.5%, and accordingly an extended run was undergone. Finally, after some 1087 seconds, oxidation was deemed complete. The total organic carbon reading was given as 129.7 parts per billion.

EXAMPLE II

| TIME (SECONDS) | TEMPERATURE (DEGREES C.) | DELTA COND @25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 4 | 28.664 | 0 | 0 | 0 | 0 | .0825 |
| 16 | 29.103 | .05908 | 0 | 0 | 2.404 | .1474 |
| 28 | 29.421 | .24178 | 0 | 0 | 17.5 | .3478 |
| 40 | 29.738 | .45866 | 0 | 0 | 50.45 | .5888 |
| 52 | 30.047 | .63815 | 1396.1 | −6.7388 | 90.06 | .7913 |
| 64 | 30.334 | .78639 | 1171.6 | −13.006 | 131.2 | .9611 |
| 76 | 30.598 | .91193 | 1006 | −12.342 | 172 | 1.1063 |
| 88 | 30.838 | 1.021 | 890.95 | −9.335 | 211.9 | 1.2342 |
| 100 | 31.056 | 1.121 | 803.74 | −7.8472 | 252.1 | 1.3523 |
| 112 | 31.253 | 1.2141 | 723.54 | −7.7782 | 292.6 | 1.4629 |
| 124 | 31.435 | 1.2977 | 629.36 | −8.4882 | 331.6 | 1.563 |
| 136 | 31.602 | 1.3683 | 517.6 | −9.2891 | 366.4 | 1.6485 |
| 148 | 31.757 | 1.4231 | 396.31 | −9.501 | 394.6 | 1.716 |
| 160 | 31.899 | 1.4625 | 277.67 | −8.9755 | 415.5 | 1.7657 |
| 172 | 32.033 | 1.488 | 173.31 | −7.8684 | 429.3 | 1.7993 |
| 184 | 32.16 | 1.5016 | 86.776 | −6.4571 | 436.8 | 1.8195 |
| 196 | 32.279 | 1.5063 | 18.624 | −5.0622 | 439.4 | 1.8289 |
| 208 | 32.391 | 1.5042 | −32.277 | −3.8177 | 438.2 | 1.8303 |

TOC CASE #3 ANALYSIS BEGINS ##

| TIME (SECONDS) | TEMPERATURE (DEGREES C.) | DELTA COND @25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 220 | 32.498 | 1.4969 | −69.678 | −2.8059 | 434.2 | 1.8255 |
| 232 | 32.601 | 1.4861 | −96.476 | −2.038 | 428.3 | 1.8166 |
| 244 | 32.699 | 1.4729 | −116.06 | −1.4334 | 421.1 | 1.8046 |
| 256 | 32.794 | 1.4578 | −130.1 | −1.0296 | 413 | 1.7903 |
| 269 | 32.892 | 1.44 | −139.92 | −.72141 | 403.5 | 1.7728 |
| 281 | 32.979 | 1.4224 | −146.93 | −.46426 | 394.2 | 1.755 |
| 293 | 33.063 | 1.4043 | −151.41 | −.26591 | 384.8 | 1.7368 |
| 305 | 33.144 | 1.3859 | −152.85 | −.099304 | 375.3 | 1.7177 |
| 317 | 33.223 | 1.3673 | −152.68 | .033286 | 365.9 | 1.6986 |
| 329 | 33.3 | 1.349 | −151.69 | .086197 | 356.7 | 1.6795 |
| 341 | 33.374 | 1.331 | −149.81 | .11268 | 347.8 | 1.6606 |
| 353 | 33.446 | 1.313 | −148.71 | .10928 | 339 | 1.6417 |
| 365 | 33.516 | 1.2954 | −147.27 | .094006 | 330.5 | 1.623 |

DEVIATION = .84375617%
EXTENDED OXIDATION IN PROGRESS

| TIME (SECONDS) | TEMPERATURE (DEGREES C.) | DELTA COND @25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 379 | 33.595 | 1.2746 | −146.23 | .10703 | 320.6 | 1.6011 |
| 391 | 33.662 | 1.2574 | −145.11 | .10531 | 312.5 | 1.5825 |
| 403 | 33.726 | 1.2399 | −143.36 | .14621 | 304.4 | 1.5638 |
| 415 | 33.789 | 1.2229 | −142.01 | .1637 | 296.6 | 1.5455 |
| 427 | 33.85 | 1.2058 | −139.21 | .16905 | 288.9 | 1.5271 |
| 439 | 33.91 | 1.1892 | −137.25 | .18477 | 281.5 | 1.5091 |
| 451 | 33.97 | 1.1731 | −135.25 | .15184 | 274.4 | 1.4915 |
| 463 | 34.027 | 1.157 | −133.14 | .14777 | 267.4 | 1.474 |
| 475 | 34.084 | 1.1409 | −131.92 | .15438 | 260.5 | 1.4566 |
| 487 | 34.139 | 1.1253 | −130.16 | .16125 | 253.9 | 1.4393 |
| 499 | 34.193 | 1.1098 | −127.84 | .18818 | 247.4 | 1.4223 |
| 511 | 34.246 | 1.0945 | −125.4 | .22807 | 241.1 | 1.4054 |
| 523 | 34.299 | 1.0796 | −122.89 | .25882 | 235 | 1.389 |
| 535 | 34.351 | 1.0651 | −119.21 | .26757 | 229.2 | 1.373 |
| 547 | 34.401 | 1.508 | −115.41 | .31109 | 223.5 | 1.3574 |
| 559 | 34.45 | 1.0373 | −112.55 | .29948 | 218.2 | 1.3423 |
| 571 | 34.498 | 1.0242 | −107.96 | .28752 | 213.1 | 1.3277 |
| 583 | 34.546 | 1.0111 | −104.84 | .3088 | 208.1 | 1.3135 |
| 595 | 34.591 | .99898 | −101.61 | .27344 | 203.5 | 1.2998 |
| 607 | 34.638 | .98697 | −97.732 | .28266 | 199 | 1.2865 |
| 619 | 34.682 | .97538 | −94.831 | .30421 | 194.7 | 1.2737 |
| 631 | 34.727 | .9642 | −91.272 | .28993 | 190.6 | 1.2615 |
| 643 | 34.77 | .95346 | −87.011 | .31068 | 186.7 | 1.2495 |
| 655 | 34.813 | .94316 | −83.815 | .30744 | 183 | 1.2382 |
| 667 | 34.856 | .93361 | −79.918 | .27943 | 179.6 | 1.2274 |
| 679 | 34.896 | .92397 | −76.514 | .30012 | 176.2 | 1.2169 |
| 691 | 34.937 | .9151 | −73.599 | .28309 | 173.1 | 1.207 |
| 703 | 34.978 | .90644 | −69.409 | .29067 | 170.1 | 1.1975 |
| 715 | 35.018 | .89828 | −66.33 | .28422 | 167.3 | 1.1885 |
| 727 | 35.057 | .89065 | −62.562 | .2659 | 164.7 | 1.1801 |
| 739 | 35.095 | .88326 | −59.956 | .25875 | 162.2 | 1.1722 |
| 751 | 35.134 | .87641 | −56.646 | .23868 | 159.9 | 1.1646 |
| 763 | 35.172 | .86951 | −53.91 | .24354 | 157.6 | 1.1573 |
| 775 | 35.209 | .86346 | −51.105 | .22194 | 155.6 | 1.1506 |
| 787 | 35.245 | .85738 | −48.266 | .21282 | 153.6 | 1.144 |
| 799 | 35.283 | .85188 | −45.993 | .20338 | 151.8 | 1.138 |
| 811 | 35.318 | .84634 | −43.695 | .19372 | 150 | 1.1322 |
| 823 | 35.353 | .84139 | −41.343 | .19689 | 148.4 | 1.1268 |
| 835 | 35.389 | .83641 | −38.968 | .2 | 146.8 | 1.1217 |
| 847 | 35.423 | .83203 | −36.542 | .1891 | 145.4 | 1.117 |
| 859 | 35.457 | .82763 | −34.095 | .17801 | 144 | 1.1125 |
| 871 | 35.491 | .82385 | −32.266 | .1527 | 142.8 | 1.1083 |

-continued

EXAMPLE II

| TIME (SECONDS) | TEMPERATURE (DEGREES C.) | DELTA COND @25° C. (MMHOS/CM) | DC/DT 1E-5 (MMHOS/DM/SEC) | D2C/DT2 1E-5 (MMHOS/CM/SEC2) | REAL-TIME TOC (PPB) | RAW COND (MMHOS/CM) |
|---|---|---|---|---|---|---|
| 883 | 35.525 | .82004 | −30.423 | .1411 | 141.6 | 1.1045 |
| 895 | 35.557 | .81654 | −29.213 | .14287 | 140.5 | 1.1007 |
| 907 | 35.59 | .81303 | −27.322 | .13053 | 139.4 | 1.0974 |
| 919 | 35.623 | .80982 | −25.409 | .14584 | 138.4 | 1.094 |
| 931 | 35.655 | .80693 | −24.158 | .11908 | 137.5 | 1.091 |
| 943 | 35.687 | .80435 | −22.213 | .10627 | 136.7 | 1.0885 |
| 955 | 35.719 | .80143 | −21.606 | .10726 | 135.8 | 1.0858 |
| 967 | 35.751 | .79916 | −20.308 | .094208 | 135.1 | 1.0834 |
| 979 | 35.782 | .79656 | −19.009 | .10904 | 134.3 | 1.0812 |
| 991 | 35.812 | .7946 | −17.691 | .095525 | 133.7 | 1.0792 |
| 1003 | 35.842 | .79231 | −16.372 | .096291 | 133 | 1.0772 |
| 1015 | 35.871 | .79067 | −15.722 | .082606 | 132.5 | 1.0755 |
| 1027 | 35.901 | .7887 | −14.387 | .083251 | 131.9 | 1.0739 |
| 1039 | 35.931 | .78705 | −13.726 | .08362 | 131.4 | 1.0724 |
| 1051 | 35.959 | .7854 | −12.376 | .069766 | 130.9 | 1.071 |
| 1063 | 35.988 | .78408 | −11.709 | .070063 | 130.5 | 1.0699 |
| 1075 | 36.018 | .78276 | −11.039 | .056074 | 130.1 | 1.0687 |
| 1087 | 36.046 | .78143 | −10.363 | .056326 | 129.7 | 1.0677 |

OXIDATION COMPLETE ##
TOC = 129.7 PPB

Figure 15:
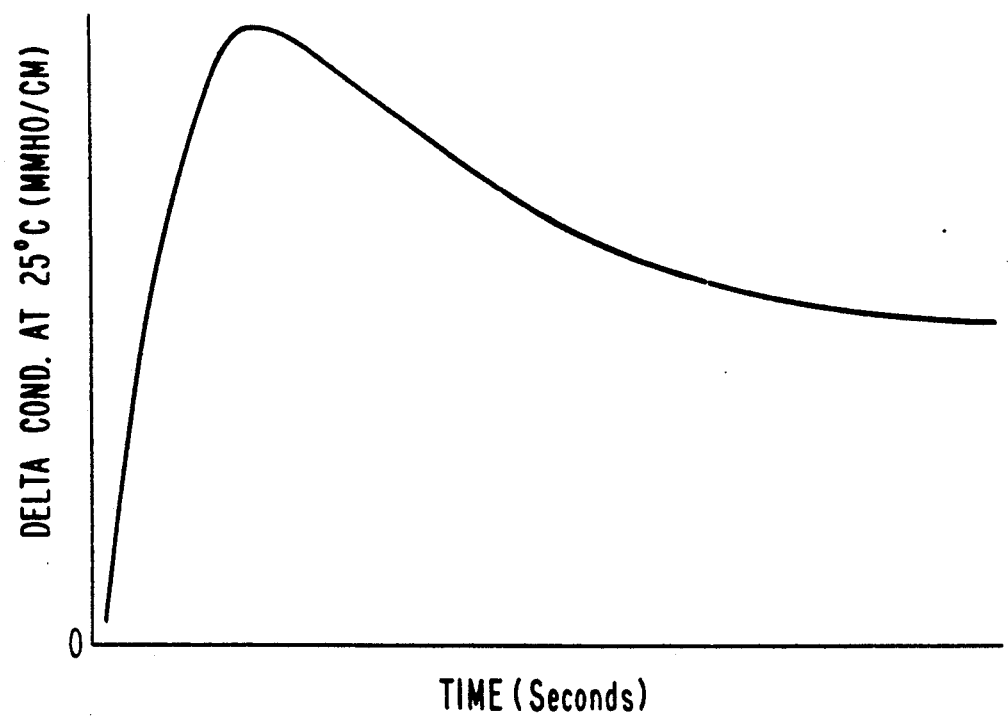
FIGS. 15-17 show actual test results.
Figure 16:
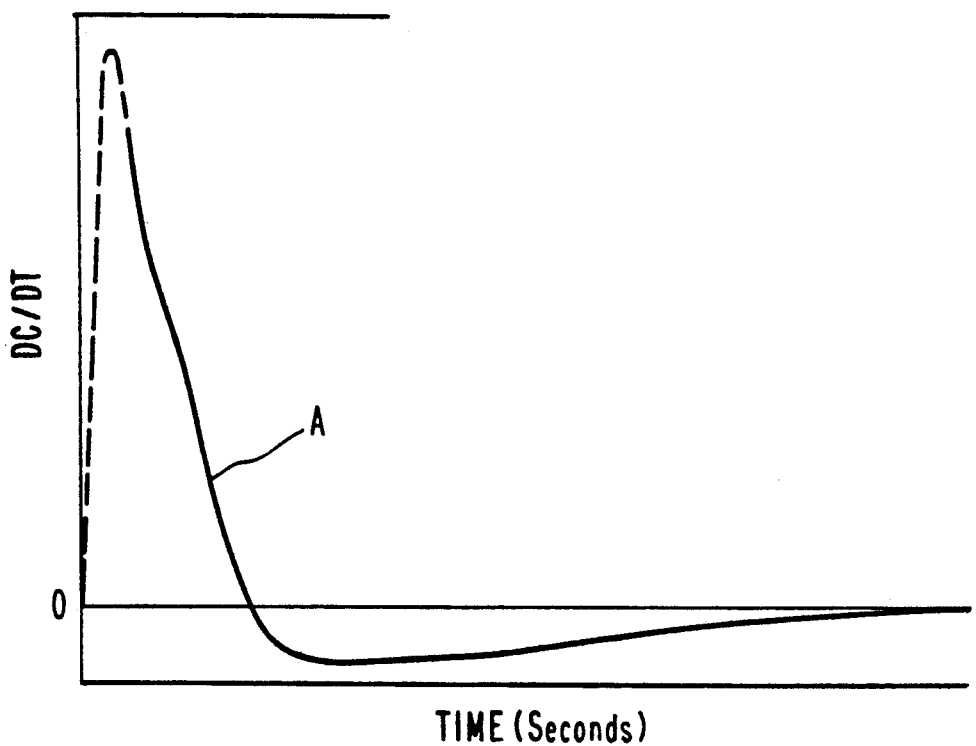
Figure 17:
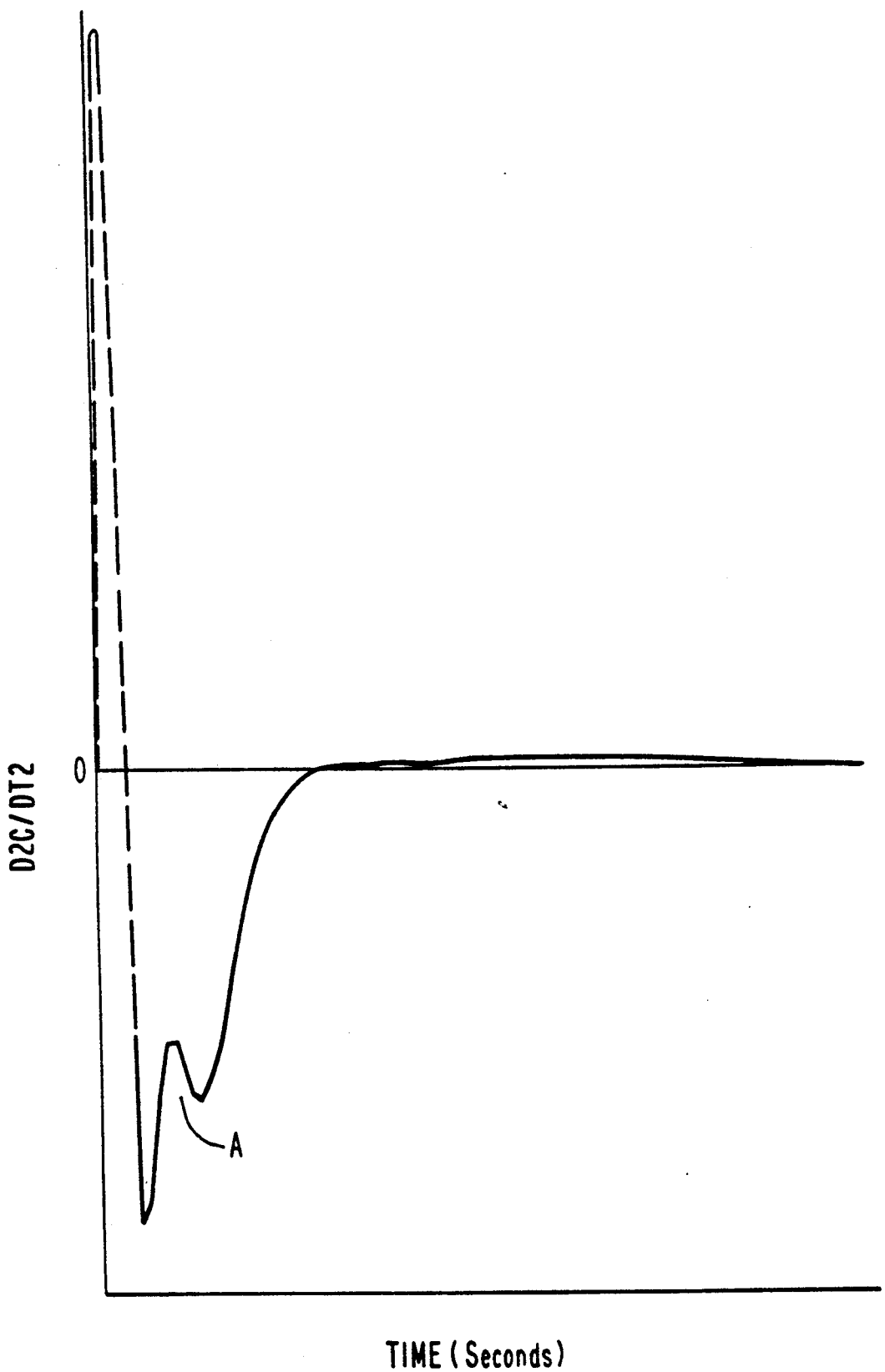

FIGS. 15, 16 and 17 show the data of Example II, plotting respectively conductivity and the first and second time derivatives thereof versus time. The dotted lines in FIGS. 16 and 17 were added by interpolation; as mentioned, data for the first few values of the first and second derivatives are not calculated by the computer program used to generate the data of Example II and the remainder of the plots of FIGS. 16 and 17. The characteristic Case III shape is very clear. The extra peak at A in FIG. 17 correctly reflects the additional inflection points at A of FIG. 16. These are believed due to local thermal variations or the like. The contaminant used for this test was acetone, supplied in the amount of 129.7 parts per billion; and the results indicated in Example II show that this result was correctly obtained.

It will be appreciated that there has been described an instrument for measurement of the total organic carbon content of water. As discussed, accurate measurement of the total organic content requires compensation for temperature-induced changes in conductivity since conductivity varies very strongly in dependence on temperature, as described in the article by Poirier et al referred to above. Further, it will be appreciated that measurement of the conductivity of water caused by oxidation of total organic matter is made possible according to the instrument of the invention by its ability to differentiate the change in conductivity occasioned by oxidation of the organic matter to carbon dioxide from the instrument contribution to the change. Therefore, the residual conductivity, that is, as measured in Phase I of the plot of FIG. 13, is an indication of the ionic conductivity of the water.

It will also be appreciated that the instrument of the invention, as already described, is effectively an instrument for measuring ionic conductivity and sample temperature as well as total organic carbon content, and it should be appreciated that such a three-function instrument explicitly providing this output data is within the scope of the claims of this application.

Reference has been made throughout this application to measurement of the conductivity between the electrodes of the cell. This must be accomplished with accuracy. Those skilled in the art will recognize that this is not necessarily a simple task. According to the preferred embodiment of the invention, this is accomplished as discussed in U.S. patent application Ser. No. 689,271, filed Jun. 9, 1985, now U.S. Pat. No. 4,683,435, incorporated herein by reference. As discussed above, according to the present invention, the sample cell, in which conductivity is measured, is also the cell in which the ultraviolet irradiation and oxidation takes place. Those skilled in the art will recognize that when ultraviolet radiation falls upon the electrodes (as desired according to the present invention, to eliminate fouling and the like) the photoelectric and photoionic effects will cause the cell to act as a battery, effectively impressing a DC voltage across the electrodes. This biases the AC signal which is conducted through the sample, and appropriate correction must be made. For reasons discussed in the Blades U.S. Pat. No. 4,683,435 referred to above, simple filtering of the DC component is not possible.

According to the preferred embodiment, and as discussed in the Blades U.S. Pat. No. 4,683,435, the cell is used in an active feedback loop which generates a DC voltage to compensate for the "battery voltage" impressed between the cell electrodes. The AC signal placed on one electrode, transmitted through the water sample and detected on the other electrode, is also compensated in the feedback loop for nonlinearities caused by other circuit elements, to provide a linear output with respect to conductivity across the cell.

Figure 18:
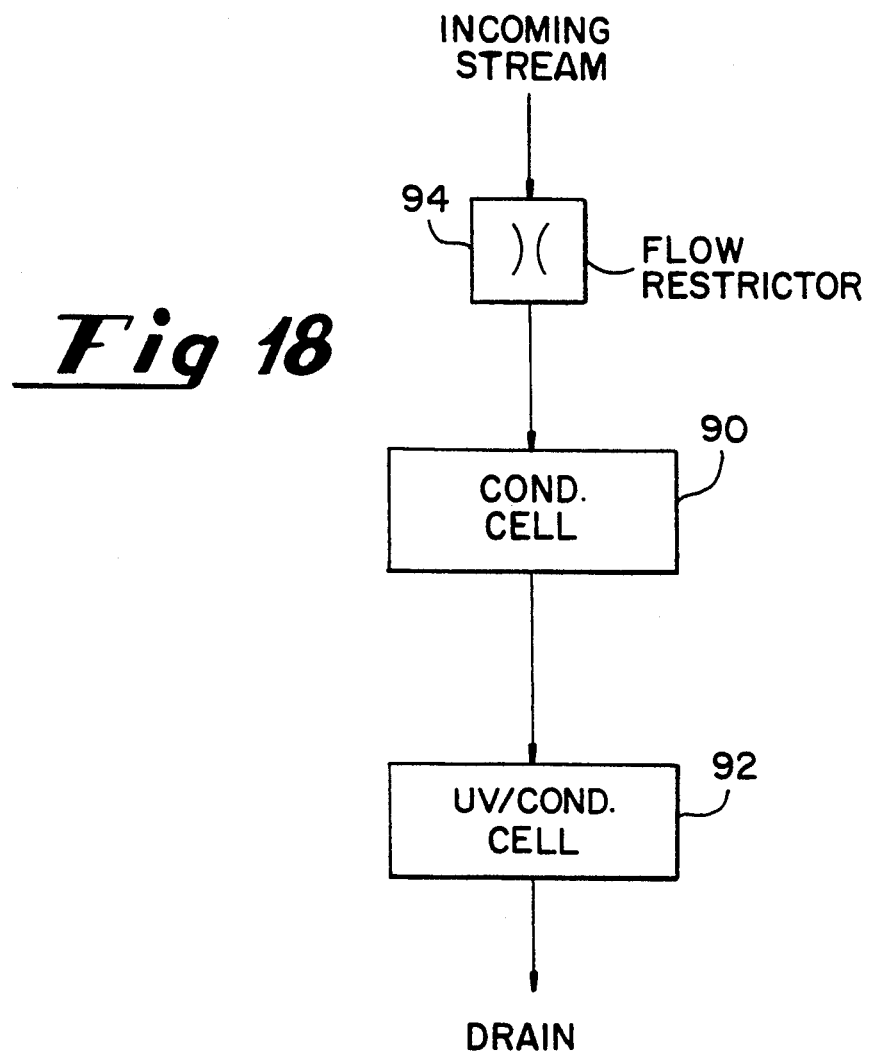
FIG. 18 shows a system for real-time monitoring of sudden changes in the total organic carbon content of a water stream.

As discussed above, the time for the oxidation reaction to go to completion is typically a matter of minutes, sometimes as many as ten to twenty, depending on the contaminant involved, the intensity of the radiation and other variables. FIG. 18 shows a system monitoring the total organic carbon content of a water stream substantially continuously, i.e., in "real time", so that for example an alarm could be triggered if a sudden change in the organic content was detected. This system comprises two sample cells in series. An upstream sample cell 90 does not include an ultraviolet lamp. A second downstream cell 92 includes a continuously-running ultraviolet lamp. The conductivity signals provided by the pairs of electrodes in cells 90 and 92 is continuously monitored. A flow restrictor 94 is installed upstream to ensure that the flow rate is constant, typically 0.2 liters per minute. The upstream cell 90 may be mechanically and electrically identical to that described in connection with FIGS. 11 and 12 (or to that described below in conjunction with FIG. 21), but because the first cell has no lamp, no oxidation of total organic carbon takes place. Hence, the output of cell 90 is indicative of the background ionic conductivity of the sample. The second cell 92 is as described above in connection with FIG. 11, and the lamp is continuously turned on.

Partial oxidation of the organic materials in cell 92 leads to generation of some $CO_2$ and/or conductive organic intermediaries, and hence to a net change in conductivity. Accordingly, the difference in the conductivity signals from the two cells is indicative of the amount of total organic carbon in the water sample, even though the organics in the sample are not fully oxidized during the short residence time of the sample in the downstream cell. Thus, while it would not be appropriate to rely on the signal from the second cell 92 for an absolute value of the total organic carbon content of the water stream, the difference between the two signals can be monitored, and any sudden changes in the value of the difference are indicative of sudden changes in the organic content of the stream, which will typically be cause for alarm. Further, at these or other times, of course, the second cell 92 can be used in the mode described above, i.e. for an extended run to determine the actual level of organics in the system, simply by shutting a valve downstream of the second cell 92 and monitoring the oxidation reaction to completion.

It will be appreciated that because the organics in the continuously flowing stream are only partially oxidized, the amount of change in conductivity resulting from the partial oxidation is dependent on the sample flow rate. Therefore, to obtain repeatable results, the flow rate must either be maintained constant by flow restrictor 94, or must be measured and the signal compensated accordingly.

It will be further appreciated that there will be a tendency for the electrodes of the first cell 90, without an ultraviolet lamp, to foul with time, and that this will affect the accuracy of the background measurements. This can be corrected for by compensation of the background value by periodically turning off the UV lamp of the second cell 92, the electrodes of which will have been kept clean by ultraviolet radiation, and adjusting the value provided by the first cell 90 to equal that provided by the second cell 92, providing appropriate compensation for results received thereafter. Alternatively an ultraviolet lamp could be provided in the first cell 90 and operated intermittently to "burn off" any accumulated organics.

Referring again to discussion of the instrument of the invention in its FIG. 11 embodiment, and according to additional understanding gained by the inventors in the interim between the filing of the first continuation-in-part application (now U.S. Pat. No. 4,666,860) and the second continuation-in-part application (now U.S. Pat. No. 4,868,127), it appears that the surfaces of the Ti electrodes in the cell are oxidized, forming titanium dioxide ($TiO_2$), and that this material provides a catalytic surface at or near which organic species are readily oxidized. It appears that the effect is due to photocatalysis, involving an interaction of UV light at the appropriate wavelength and the $TiO_2$ surface.

This discovery was made when the inventors were testing their instrument in connection with a water sample having less than one part per billion dissolved oxygen. They had expected to see the response drop as the oxygen content dropped, because their understanding was that a typical reaction, e.g. for the oxidation of methane, was simply $$CH_4 + 2O_2 \rightarrow CO_2 + 2H_2O$$

Hence, as the oxygen content of the water was reduced, a corresponding reduction in the oxidation was anticipated, as two oxygen molecules would be required to oxidize each CH molecule to $CO_2$. However, in fact the instrument responded substantially identically, whether or not the water was deoxygenated. Further study indicates that the source of oxygen was hydroxyl (OH) radicals generated from the water itself due to a photocatalytic effect occurring at the titanium dioxide surface caused by the incident UV radiation.

Conventional total organic carbon analyzers operating on low oxygen content water or on waters containing organics which are relatively refractory, that is, difficult to oxidize, have required the addition of oxidizers, e.g., potassium persulfate, to the sample. Either ultraviolet light or heating then causes the potassium persulfate to produce hydroxyl radicals.

Unfortunately potassium persulfate solutions are not stable for more than a few weeks or months. They are decomposed by both light and heat. Therefore, they must be replaced frequently in laboratory equipment. Furthermore, the use of such reagents introduces other variables which may not be easy to control, particularly in connection with low-level TOC analysis. By comparison, the inventive use of the titanium dioxide/ultraviolet radiation photocatalysis system allows production of highly oxidative hydroxyl radicals from the water itself.

Some research has been done into the area of photocatalytic reduction of organic compounds, specifically in connection with long-wavelength ultraviolet light or visible light irradiating N-type semiconductor surfaces such as titanium dioxide. See, for example, "Organic Heterogeneous Photocatalysis: Chemical Conversions Sensitized by Irradiated Semiconductors", Fox, *Acc. Chem. Res.* 1983, pp. 314–321; Arakawa, "The Present Status and Trends of Photocatalytic Reactions", *TechnoJapan* Vol. 18-11, Nov. 1985, pp. 10–22. For example, on page 21 of the *TechnoJapan* article Arakawa states that "Organic halides in an aqueous solution can be decomposed by 300–400 nm near ultraviolet rays in the presence of a $TiO_2$ catalyst". The inventors have, however, found no reference to use of such techniques in connection with organic carbon analysis. Further, no reference appears to recognize the very important distinction realized by the inventors in connection with the wavelength of the UV light used. The 300–400 nm radiation discussed by Arakawa provides energy sufficient to "pump" the N-type semiconductor $TiO_2$ to its active state. That is, 300–400 nm near-UV removes electrons from the semiconductor surface, providing a positively charged surface which attracts the $OH^-$ ions and charged ionic organic intermediates, thus catalyzing their oxidation. The inventors find that while shorter wavelength UV specifically of 253.65 nm or 184.97 nm wavelength also activates the $TiO_2$, UV radiation of these frequencies also helps to break up the organics so that their components can then be readily oxidized. The UV radiation at these wavelengths appears to break up organic compounds, such as acetone, to acidic ions, such as acetic acid. The acids, being ionized, are then attracted to the charged TiO₂ surfaces where they are readily oxidized by combination with the OH radicals.

It will be appreciated that the use of a solid state catalytic surface such as titanium dioxide is highly advantageous as opposed to adding additional oxidizers such as perchlorates. The reaction rate is greatly improved, as will be detailed below, yet no additional chemicals involving additional contamination need be added.

As described briefly above, it appears that the mechanism of the enhanced oxidation of organics provided by photocatalysis at the titanium dioxide electrode surface by ultraviolet radiation involves oxidation using oxygen provided by hydroxyl (OH) radicals. These are produced by disassociation of water into hydronium ($H_3O^+$) and hydroxyl ($OH^-$) ions. As is well known, at any given temperature, some fraction of water molecules undergo "autodisassociation". The titanium dioxide semiconductive surface, which is positively charged due to the photoelectric effect when the UV radiation is incident thereon, then provides an attractive coupling site for the hydroxyl ion. Once the hydroxyl ion is in contact with the surface, the UV and semiconductor cooperate to remove the electron from the $OH^-$ ion, forming an OH radical at its surface. This radical is believed by the inventors to be both the oxidizing agent for the destruction of the organic molecule and a source of oxygen in low oxygen content waters. It will be appreciated that the formation of a hydroxyl radical in this manner is very different from the generation of hydroxyl radicals from persulfate compounds, as nothing has to be added to the water except the UV light.

As described briefly above, it is believed that oxidation of refractory organics, such as acetone or the like, begins when the UV light initially breaks these electrically neutral molecules up into charged ions. For example, acetone becomes acetic acid and formate becomes formic acid. The acids are in ionic form in solution. These ions should then be physically juxtaposed to the hydroxyl groups on the TiO₂ surface, to utilize the photocatalytic oxidation to maximum advantage. There are several ways in which the ions may be brought to the TiO₂ surface. These include electrophoresis (useful in connection with deionized water only), physical mixing, and provision of a high catalyst surface area/solution volume ratio. Mixing is undesirable as the inevitable pump, impeller, etc., will tend to introduce impurities and inconsistencies in the experimental system. Provision of a high surface-to-volume ratio is difficult where the surface area of a catalyst must be exposed to UV; it is difficult to provide an enlarged surface area, all of which is directly exposed to incident radiation from a single source. Accordingly, the inventors have experimented with electrophoresis as a means of attracting the ions to the catalytic surfaces. These experiments have been extremely successful. In practice, electrophoresis simply involves applying a voltage, typically up to 150 V, across the electrodes of the measurement cell. This is indicated schematically at V in FIG. 11. An electric field is then impressed between the electrodes, imparting a force to the ions, causing them to migrate toward the oppositely charged one of the electrodes. The voltage may be applied continually except when a conductivity measurement is desired, or a compensation for the voltage may be made to the measured value of the conductivity.

The inventors' experiments with electrophoresis indicate that solutions which take on the order of 30 minutes to react to completion without electrophoresis can typically be completely reacted in 6 minutes or less employing electrophoresis as generally described above to "drive" the ions to the reaction surface.

The inventors have also experimented with electrolysis. As is well known, in this technique a current is passed through electrodes in an aqueous solution, causing oxygen and hydrogen to be generated in the water. This of course provides an excellent source of oxygen and provides an additional increase in the rate of oxidation of even refractory organics. However, the additional hydrogen molecules in the water cause so-called back reactions, upsetting the accuracy of the conductivity measurement. Additionally, electrolysis tends to damage the electrode surfaces.

As described above, the cell design according to the invention directly exposes the surfaces of the electrodes to the incident UV radiation, so that the UV tends to "burn off" any organics that might otherwise adhere to and foul the electrodes. It will be apparent to those skilled in the art that the fouling of the electrodes, essentially biological growth and deposition of relatively nonpolar organics on the electrode surfaces, would cause deviation of the conductivity values from normal readings. These effects can include changes in the cell capacitance, altered cell constant values, sensitivity to flow rate and inaccuracy in temperature corrections.

The fouling of electrodes which occurs in conventional instruments is a grave difficulty, particularly in connection with relatively ultrapure water; as the subtlety of the measurement increases, the sensitivity of the electrodes to the conductivity of water must likewise increase if an accurate measurement is to be made. Therefore, any fouling of the electrodes in an instrument designed to measure the conductivity of ultrapure water, as is the inventors', is highly detrimental. Typical methods of cleaning electrodes exposed to organics involve rinsing with hydrogen peroxide and/or hydrochloric acid and flushing with deionized water.

The inventors' experience with the cells shown in FIGS. 1 and 11 indicates that after over two years of continuous operation, the electrodes never require this cleaning, presumably because they are photoelectrochemically cleaned continually by virtue of their exposure to the ultraviolet radiation. This has provided a great advantage to the system of the invention. Together with the fact that the instrument according to the invention is effectively self-calibrating, by virtue of the automatic compensation for the instrument contribution provided as discussed above, the avoidance of regular cleaning allows the instrument of the invention to be considered essentially maintenance-free under ordinary circumstances.

The inventors' realization that the TiO₂ surface in combination with the ultraviolet radiation provides a photocatalytic effect which is highly useful in breaking up organics, all as described above, further points out the need for the electrode surface to be exposed to UV. It will be apparent that unless the electrode surfaces are exposed to direct incident radiation, they will not be active catalytic surfaces. Therefore, an additional highly significant reason for designing the cell so that the electrodes are exposed directly to UV is realized.

As described above, the inventors' experiments reveal that organics tend to be oxidized in the cell of the invention according to one of three possible types of behavior. "Case I" behavior, in which the conductivity increases smoothly from the initial value to the final value in an asymptotic fashion, such that the final value is unchanging with time, occurs when the oxidation proceeds without the formation of organic acids or conductive organic intermediates. Methanol is an example of a compound that oxidizes according to the Case I pattern. In the "Case III" pattern, the conductivity first increases from its initial value to a value for conductivity greater than the final value, and then drops to the final value in an asymptotic fashion. This occurs when organic acids or other ionic organics are produced as temporary intermediates during the oxidation of the compounds. The "overshooting" of the conductivity reading is due to the greater conductivity of the reaction intermediates than the $CO_2$ in the final solution.

"Case II" behavior is very similar to that of Case I except that the final conductivity is not constant; that is, the first derivative of the conductivity is a non-zero positive value. As described above, the value of the first derivative of the conductivity with respect to time is constant when the reaction is completed, and can be multiplied by the total elapsed time to arrive at an estimation of the instrument conductivity component at the end of the reaction. This value can then be subtracted from the total conductivity value determined at the end of the reaction to arrive at the corrected value for the conductivity. This behavior is exhibited when the total organic carbon in the sample is sufficiently low that the instrument's background contribution is significant and must be compensated for. That is, as described in detail above, Case II behavior is exhibited when the instrument continues to make an increasing contribution to the conductivity of the solution, and is typically only seen (in a properly designed instrument) when the total organic carbon content of the sample is extremely low.

According to an important aspect of the invention described the second continuation-in-part application, now U.S. Pat. No. 4,868,127, the inventors have discovered that application of electrophoresis to the cell, in combination with the use of short wavelength UV and the $TiO_2$ catalytic surface, causes Case III reactions to proceed almost as Case I reactions. The breakup of the refractory organics into intermediates having higher conductivities than the conductivities of the fully oxidated product, that is, the Case III behavior, is effectively eliminated by the rapid oxidation of the organics which occurs when electrophoresis is applied. In such case, the Case III behavior becomes effectively Case I behavior, much simplifying the data processing techniques and clarifying the information provided by the instrument. Together with the overall speeding of the reaction rate provided by electrophoresis, this simplification of the data processing provides obvious and important advantages for the user.

In appropriate cases, such as when the contaminants do not vary the detection method can be further simplified by assuming a fixed time will be adequate for oxidation to proceed to completion. The fixed time may be a time known to be sufficient to ensure oxidation of the most refractory organics.

As mentioned above, photocatalysis of organics using near-UV radiation of 300–400 nm wavelength in combination with a $TiO_2$ surface is known. See the Arakawa article referred to above. Arakawa also teaches that other N-type semiconductive materials provide useful catalytic surfaces; those listed include $SrTiO_3$, CdS, $WO_3$, $Fe_2O_3$ and $MO_3$, all of which, like $TiO_2$, have electron band gap energies greater than 1.75 eV; this minimum energy appears to be useful in breaking up organics. The inventors have experimented with $WO_3$ in addition to $TiO_2$; $TiO_2$ appears to be more effective in the particular circumstances of the experiment.

Formation of the $TiO_2$ catalyst on the surface of the electrodes can be accomplished as follows. The electrodes are machined from solid Ti. The machined surfaces are thoroughly cleaned and decreased. The cell is then assembled. A $TiO_2$ layer is formed when the cell is filled with pure water and the electrode surfaces are irradiated by the ultraviolet radiation. If desired, a thicker layer of $TiO_2$ can be formed by heating the electrodes to approximately 800° C. in an air or oxygen-rich atmosphere.

As noted, the inventors have had extremely good results oxidizing organics with a low pressure mercury vapor lamp which is understood to produce UV at some 184.968 and 253.652 nm. A suitable lamp is the Model No. 81-1057-01 two inch "Analamp" available from BHK, Inc. of Monrovia, Calif. This lamp was chosen because it is effective and relatively inexpensive. However, it will be appreciated that other lamps could no doubt be used which produce ultraviolet radiation of somewhat different wavelengths. It would seem that any radiation in the 170–190 nm range would be of use in lieu of the 184.968 nm wavelength. Below 170 nm the water would absorb the energy. Above 190 nm the saturated organics (organics without so-called "pi bonding") will not absorb enough energy to react directly with the photons of the UV radiation. Hydroxyl radicals can be produced by light of wavelengths between 325 and 350 nm with $TiO_2$, as shown by Arakawa. Such radicals oxidize saturated organics effectively. Similarly, the 253.652 nm light causes potassium persulfate solutions to release oxidizers even in the absence of the $TiO_2$ catalyst. However, as discussed above, use of potassium persulfate or other chemical additives is undesirable.

In practice, the inventors have found that the combination of the $TiO_2$ catalyst and the short wavelength 184.968 nm and 253.652 nm radiation produces a very oxidative environment. It should be noted that the low pressure mercury vapor lamps used by the inventors emit most of their radiation at 253.652 nm and only 1–3% at 184.968 nm. For efficiency's sake, it is clearly important to use the 253.652 nm radiation insofar as possible. It appears that the catalytic $TiO_2$ surface permits this to be realized.

As indicated generally above, the instrument of the invention finds primary utility in connection with measurement of the total organic carbon content of water samples of very high purity. It is important to the practice of the invention that a substantial fraction of the $CO_2$ formed upon oxidation of the organic carbon be dissociated in the water sample, as otherwise (that is, if it is substantially gaseous the $CO_2$ will not contribute to the conductivity. This provides an effective limitation on the quantity of $H^+$ ions which may be present in the water sample prior to oxidation. The instrument is primarily intended for TOC measurements on water samples of purity equivalent to water which has been positively deionized, e.g. by passage through ion-absorbing resin beds, and some of the appended claims may be so limited. It should be understood therefore that the term "deionized water" as used herein is intended to include water of such high purity, water which has been deionized prior to TOC measurement according to the invention, and water which has at one time been deionized, but which may subsequently have absorbed some ions, typically $CO_2$, from exposure to the atmosphere.

The above discussion is essentially repeated from application Ser. No. 938,638, now U.S. Pat. No. 4,868,127. The following represents additional information and understanding gained by the inventors in the interim.

More specifically, the prior related applications identified above were directed generally to an instrument for determining the total organic carbon content of water, and had emphasized that the instrument was intended to be used with "deionized" water.

It will be appreciated by those of skill in the art that "deionized" water as thus defined is not equivalent to water having a neutral pH of 7.0, although deionized water is in fact neutral; it is possible to buffer water to pH 7.0 while it is far from deionized, that is, while the water contains substantial dissolved chemicals. "Deionized" water, as satisfactorily monitored for TOC by the instrument of the invention as described in the prior applications, must be purified water of very high resistivity (e.g. $>5$ m$\Omega$-cm). According to one aspect of the improvements disclosed and claimed in the present continuation-in-part application, the TOC content of water of somewhat lower resistivity (e.g. $>0.1$ m$\Omega$-cm) may be successfully monitored, if the principal ionic species contributing to the reduced resistivity is known, and if the water is otherwise purified, that is, substantially free of other ionic species as well as all solid contaminants and the like.

More particularly, the term "deionized" is used in the art to refer to waters having resistivities of roughly 0.1 m$\Omega$-cm or higher. Water of such high resistivity has normally been purified by reverse osmosis, removal of all solids, etc., as well as literally by deionization. Hence the conductivity of the water will normally be due to dissolved $CO_2$ or dissolved salts such as NaCl, rather than sulfuric acid or the like. For such samples, the relationship between the solubility of $CO_2$ and the conductivity of the water is well known, albeit non-linear. Accordingly, given that the sample is "deionized" as defined above, and given an initial conductivity measurement, further changes in conductivity occurring responsive to oxidation of organic carbon in the water upon exposure to UV can be accurately related to the initial TOC of the water sample.

However, it would be desirable to be able to employ the instrument of the invention to measure the TOC content of waters which are not literally "deionized" but are none the less "purified". For example, it is common in non-nuclear power plant cooling water systems to "buffer" water by addition of a small amount, typically a few ppm, of ammonia to neutralize any acid in the water and prevent corrosion. Such a buffered solution will typically have an excess of ammonia, and thus will not be "deionized"; more particularly the ammonia will alter the relationship of the solubility of carbon dioxide to the conductivity of the water sample. Accordingly it was not possible to accurately measure the TOC content of such buffered samples using the instrument of the invention as described in the prior applications.

However, the addition of ammonia (or other known buffers or other ionic additives) alters the relationship of the solubility of $CO_2$ to the conductivity of the water in a known manner. Therefore, if the identity of the additive is known, the pH of the water can be measured to determine the amount of the additive present, and this information can be employed to compensate the $CO_2$ solubility/conductivity relation to yield accurate TOC results.

Therefore, it is possible to combine an instrument for measurement of the pH of a water sample with the instrument for oxidizing TOC in the water sample and for measuring the conductivity of the water according to the invention, and use this combined instrument to determine the TOC content of a relatively wider range of waters of varying acidity or alkalinity, again given that the additive affecting the pH is known. More generally, it is possible according to this aspect of the present invention to measure the pH of a water sample and use this to correct the assumption that the solubility of $CO_2$ in the water sample is consistent from sample to sample, as was required by earlier embodiments of the invention. According to the present improved embodiment of the invention, the conductivity measurement is corrected first for temperature, then for pH, to arrive at a correct value of the actual conductivity of the water.

In the past, pH meters have been too costly to be useful in conjunction with the instrument of the invention as described in the prior applications. However, recently there have been developed relatively inexpensive pH meters involving so-called CHEMFETS, that is, field effect transistors having conductance varying upon exposure to various chemical solutions. Such a CHEMFET can be made very sensitive to minute variations in the acidity or alkalinity of a water solution and thus can be used to provide a signal equivalent to pH. This signal can be used to compensate the actual conductivity values measured by the apparatus of the invention (as shown for example in FIG. 21) in accordance with the $CO_2$ solubility/conductivity relation at that pH, to provide a correct indication of the actual amount of $CO_2$ in the water, both as free ions and dissolved in gaseous form.

According to a further aspect of the present invention, there is provided an improved method of processing the conductivity data determined by the instrument of the invention in order to determine when the particular oxidation reaction is complete. More particularly, it was discussed above that the derivatives of conductivity measurements made at intervals of time could be employed to indicate when a particular reaction had proceeded to completion. According to the prior practice of the invention, the conductivity measurements were analyzed as a function of time and the final conductivity value was converted to a value for $CO_2$ content and thus for TOC at the end of the analysis. As discussed above in detail, this "derivative analysis" essentially detects significant features in the shape of the curve, i.e. zero crossings and approach of an asymptotic limit.

The solubility of $CO_2$ in water (and thus the total $CO_2$ content) is a non-linear function of the conductivity of the water sample. Therefore, the shape of a curve depicting the measured conductivity differs from the shape of a curve of actual $CO_2$ content values if both are plotted as functions of time. Since it is the oxidation of the TOC to carbon dioxide which is actually to be monitored to determine the end of the reaction, it is more meaningful to employ equivalent $CO_2$ content values derived from the conductivity values measured than the conductivity values themselves, and this is now the preferred embodiment of the invention.

Figure 19:
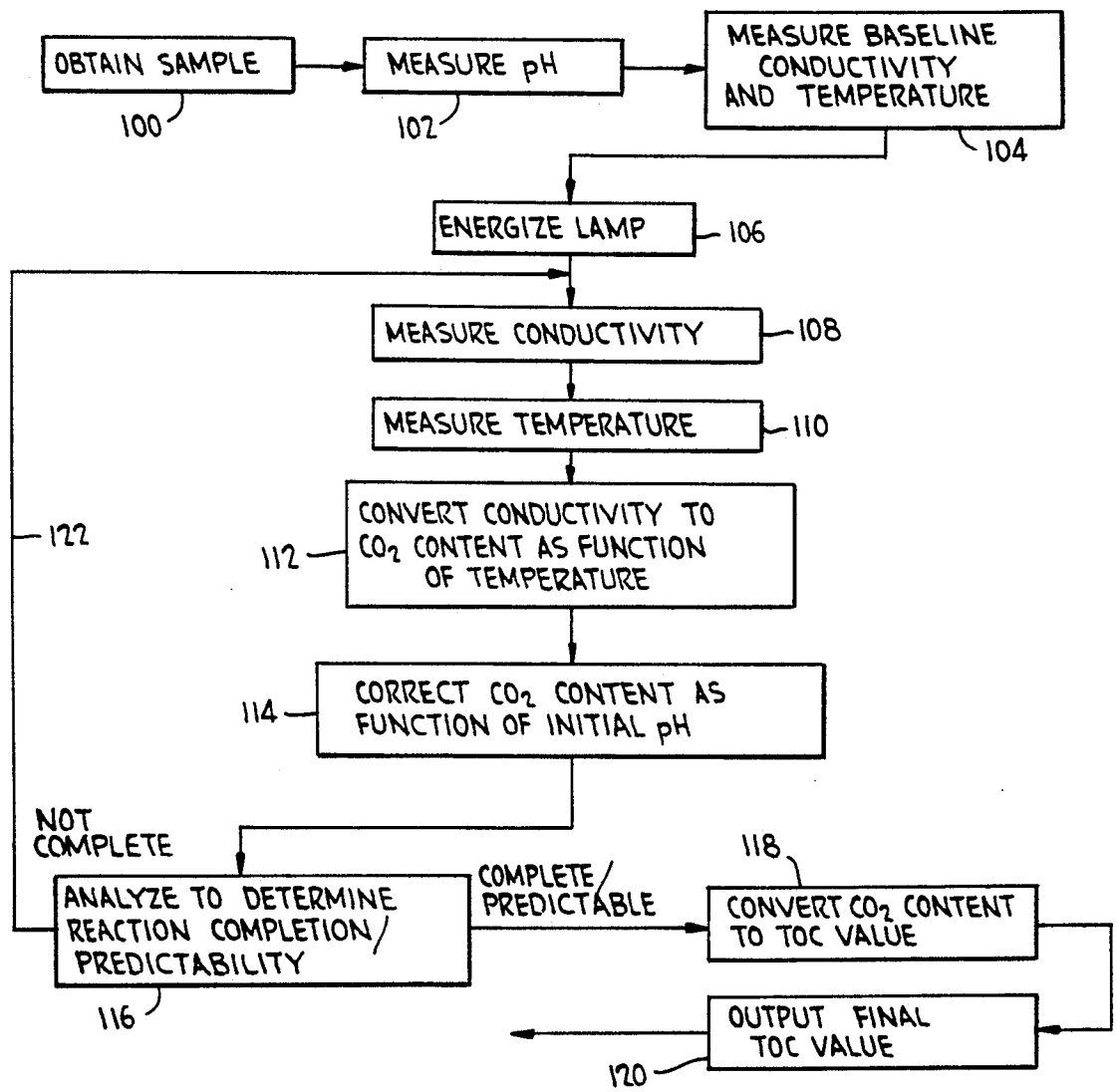
FIG. 19 shows a flowchart of analytical steps performed in the presently preferred method of the inventions.
Figure 20:
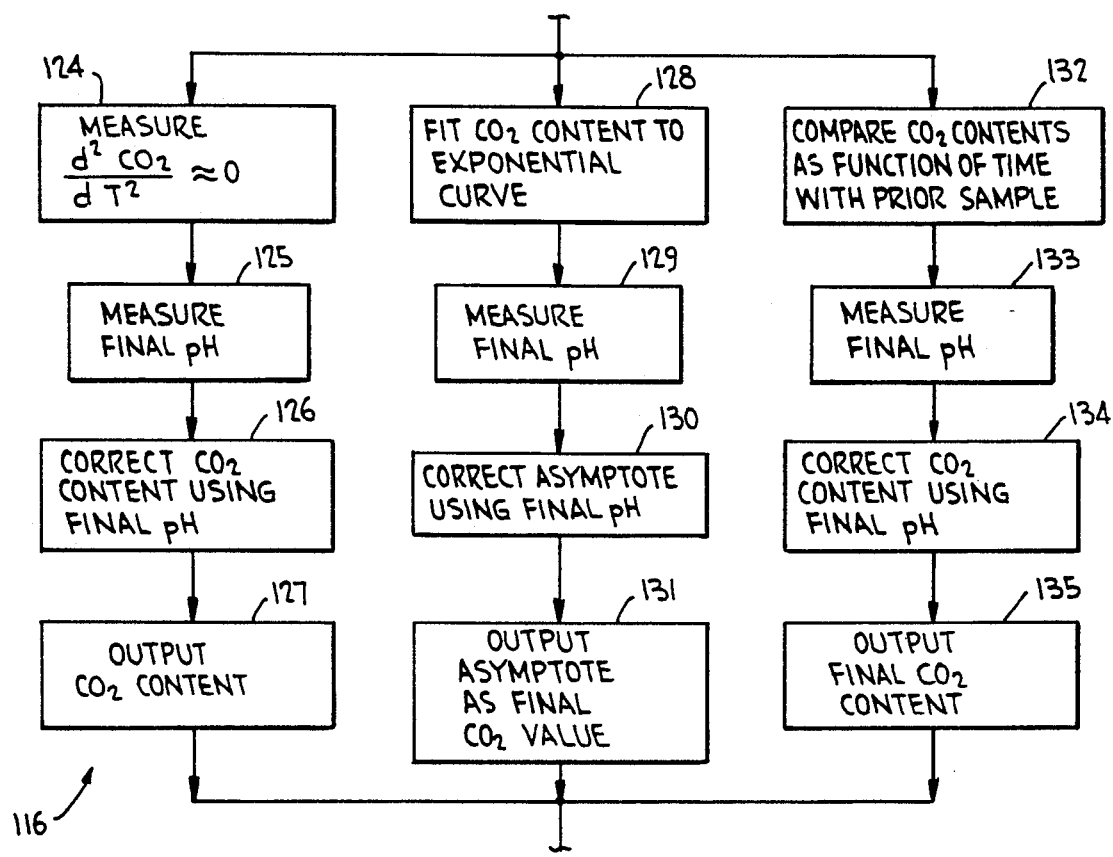
FIG. 20 shows optional steps performed in on of the steps of the flowchart of FIG. 19.

FIGS. 19 and 20 provide flowcharts illustrating the preferred methods of analysis of the measured values for the conductivity of the water sample. These methods assume that the sample may include an unknown amount of a known ionic species, e.g. ammonia, and accordingly the pH is measured and used to compensate the $CO_2$ solubility/conductivity relation. If the sample is in fact highly resistive deionized water, these steps are dispensed with.

As illustrated in FIG. 19, a typical analysis process begins at 100 when a sample is obtained. The pH of the sample is measured at 102. The conductivity and temperature are measured to establish baseline values therefor at 104. The ultraviolet lamp is then energized at 106. In a repetitive process, the conductivity is measured at 108, the temperature is measured at 110 and the conductivity value measured is converted to a value for equivalent $CO_2$ content as a function of the measured temperature at 112. According to one aspect of the present invention, the equivalent $CO_2$ content value is then corrected as a function of pH, at 114. Accordingly, the sample need not be deionized per se; that is, if the overall chemistry of the sample is generally known, the pH of the sample is measured in order that the measured conductivity value can be accurately converted to a value for the carbon dioxide content of the sample. At 116 the sequence of values for the $CO_2$ content of the sample is analyzed to determine whether the reaction has either been completed or is predictable. This analysis is carried out as discussed below in connection with FIG. 20. If the reaction is complete or predictable, the final value for the $CO_2$ content of the sample can be converted to a value for the total organic carbon content of the initial sample at 118 and a TOC value can be output at 120. If the analysis step 116 indicates that the reaction is neither complete nor yet predictable, steps 108, 110, 112, 114 and 116 are repeated as indicated at 122.

It will be apparent to those of skill in the art that increasing the sampling rate improves the accuracy of the analysis. In a currently preferred embodiment of the invention, the sampling rate is 5/second. The accuracy of the analysis can further be improved by noise filtering, preferably using an exponentially weighted running average technique.

As indicated FIG. 20 shows details of the analysis step 116. FIG. 20 represents three optional methods to determine whether a particular reaction is complete or has become predictable. Each of these can be employed in connection with analysis of the same sample if desired. For example, at step 124 the second time derivative of the $CO_2$ content is compared to zero. This analysis is a discussed above in detail except that according to the present invention the $CO_2$ content of the sample rather than its conductivity per se is monitored. When the second time derivative of the $CO_2$ content is within a certain minimum value near zero, the $CO_2$ content can be corrected at 126 responsive to a measurement of pH typically carried out at 125 after the reaction is complete. The corrected $CO_2$ content can be output at 127 and converted to a TOC value at 118.

As the variation in conductivity due to change in the $CO_2$ content and the variation in pH due to the same source are not directly related, measuring the pH after completion of the reaction provides a useful correction to the $CO_2$ content values. If the contaminant contributing to the pH is known, the correction can be made exact.

In a second alternative, the series of values for the $CO_2$ content of the sample, measured as discussed above, can be fit to an exponential function. That is to say, as a given reaction proceeds to completion, the $CO_2$ content of the sample will increase at a decreasing rate, so that as the reaction proceeds to completion, the $CO_2$ content reaches an asymptotic limit. If the values can be fit to an exponential curve at step 128, the asymptote can be predicted without carrying the reaction to completion. Again, the value of the asymptote is corrected at 130 responsive to a final pH measurement carried out at 129 so that at step 131 the corrected value of the asymptote approached by the exponential curve can be output as the final $CO_2$ value.

In a further alternative the series of $CO_2$ values can be compared at 132 to values measured at corresponding stages of a previous reaction involving a similar sample. If the $CO_2$ content of a present sample varies over time in substantially the same manner as the $CO_2$ content of a prior sample, it can be safely assumed that the ultimate value for the $CO_2$ content will be identical. Thus at 135 the value for the final $CO_2$ content of the prior sample can be output as the final $CO_2$ content of the present sample, without requiring that the reaction proceed to completion. Again the final value of the equivalent $CO_2$ content is corrected at 134 responsive to a final measurement of pH at 133. Obviously when the instrument of the invention is used for repetitive monitoring of successive samples from the same process this option will be useful.

Referring in detail to the second analytical alternative, fitting the sequence of $CO_2$ content values to an exponential curve, applicants have gained certain additional understanding of the dynamics of the reaction of interest to those of skill in the art. It is discussed above that various organic compounds are oxidized in different ways characterized above as Types I, II and III. Each of these classes of compounds are oxidized to $CO_2$, but certain compounds may react to become intermediates before they are finally oxidized to $CO_2$. The intermediates may include nonconductive species such as formaldehyde and simple alcohols (characterized by Type I behavior), weakly conductive series such as formic acid (Type II), or strongly conductive species such as acetic acid (Type III).

The inventors have found that if the TOC level is sufficiently low that the reaction rate conforms to first degree kinetics (meaning that ample oxidants are present) each of these systems can be modeled by numerical curve fitting to a simple exponential curve. Typically curve fitting is possible when the reaction is 95-99.5% complete, commonly saving up to 40-60% of the total reaction time. It has been found furthermore that even when the catalyst forms the primary reaction site, first degree kinetics provides an accurate model allowing the completion of the reaction to be modeled using a simple exponential function, again given that the TOC concentration is sufficiently low that the catalyst provides an abundance of reaction sites.

It can thus be seen that according to one currently preferred embodiment of the invention, the measured conductivity values are converted to values for the equivalent carbon dioxide content of the water sample. That is, at any particular combination of resistivity and temperature of the water sample, a known fraction of any given percentage of carbon dioxide in the water will be dissolved as ionic species, contributing to its conductivity, while the remainder will be dissolved as gas and will not contribute to the conductivity. Moreover, if a portion of the conductivity of the sample is due to the presence of a known ionic species, that species can be measured using a suitable pH sensor, and its contribution to the conductivity employed to compensate the measured value thereof. According to this aspect of the present invention, the pH of the water sample is directly measured before the oxidation begins, and the temperature is measured repeatedly. The measured values of the conductivity are corrected to give a true value for the total carbon dioxide content of the water sample, that is, including both gaseous and ionized portions, and these $CO_2$ content values are analyzed to provide an accurate value for the amount of total organic carbon in the water sample. The $CO_2$ content can also be corrected responsive to a second measurement of the pH of the water sample at completion of the analysis.

Figure 21:
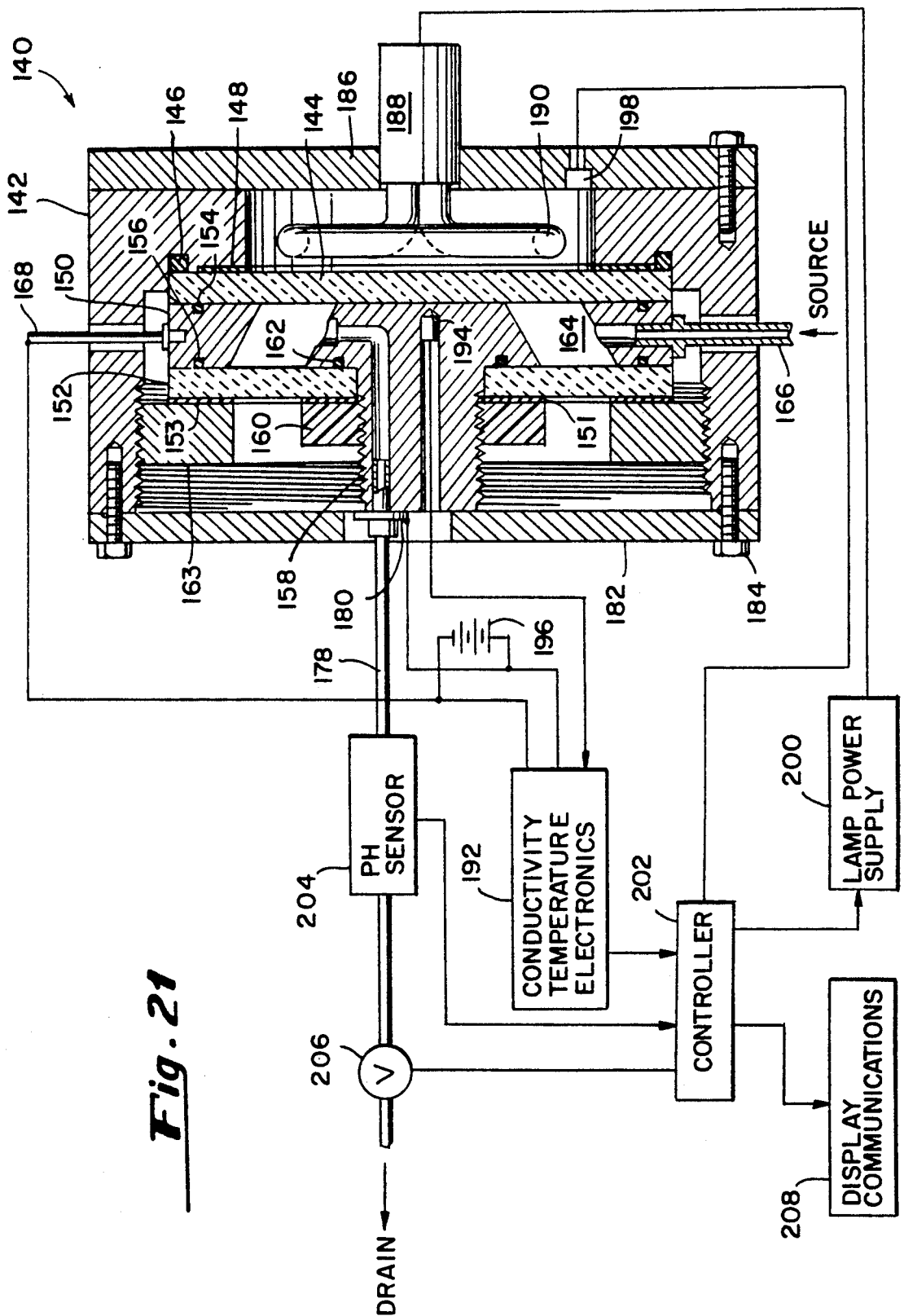
FIG. 21 is a schematic view of the system of the invention including a cross sectional view of the sample cell in the presently preferred embodiment.

FIG. 21 shows the system of the invention in its currently preferred embodiment, including a cross-sectional view of the sample exposure and analysis cell. The cell 140 comprises a body member 142 which is generally cylindrical and may be formed of aluminum. The cell body 142 has a generally cylindrical recess therein into which each of the principal components of the cell are assembled in sequence. The cell body 142 receives a circular quartz window 144 sealed to the body 142 by an O-ring 146 and spaced therefrom by a Teflon washer 148. A circular outer electrode 150 follows, and is sealed to the quartz window 144 and a ceramic backing member 152 by O-rings 154 and 156 respectively. An inner electrode 158, also generally circular, is assembled to the ceramic backing member 152 and secured thereto by a Delrin nut 160 threaded over a stem portion of the inner electrode. A further O-ring 162 seals the inner electrode 158 to the ceramic backing member 152. An externally threaded locking ring 163 mates with an internal thread formed on the inner diameter of the body 142 of the cell to secure the assembly together. Teflon washers 151 and 153 may be provided to ensure that the ceramic backing member 152 does not gall against the Delrin nut 160 or locking ring 163.

Water enters an annular chamber 164 formed between the outer electrode 150, the inner electrode 158, the quartz window 144, and the ceramic backing member 152 via an inlet fitting 166 threaded directly into the outer electrode 150. A first electrical connector 168 is similarly threaded into the outer electrode 150.

Water leaves the chamber 164 by way of a second fitting 178 threaded directly into the stem of the inner electrode 158. A second electrical connection may be secured to a washer 180 secured to the inner electrode by the fitting 178.

A rear cover member 182 is held to the body 142 of the cell 140 by screws 184. A front cover plate 186 retains an ultraviolet lamp 188. In the currently preferred embodiment, the lamp 188 includes a circular section 190 situated so that radiation from the circular section 190 of the lamp 188 illuminates the facing surfaces of the outer electrode 150 and the inner electrode 158 forming walls of the annular chamber 164. Both electrodes are formed of titanium, and their active surfaces preferably are formed of $TiO_2$, which is photocatalytically active when exposed to UV as discussed above. Direct exposure of the active TiO, electrode surfaces to UV promotes oxidation of TOC in the water sample to carbon dioxide by the catalytic reaction discussed above and also prevents the electrodes from becoming fouled with organic matter and the like.

The outer electrode 150 and the inner electrode 158 are connected to a conductivity/temperature electronics unit 192 to compensate the measured values of the conductivity for the temperature of the water sample. The temperature of the water sample is measured by a sensor 194 disposed in a recess in the inner electrode 158 in close juxtaposition to the window 144 so as to accurately detect the temperature of water within chamber 164. If desired, a DC voltage indicated schematically by a battery 196 may be impressed across the inner and outer electrodes for electrophoretic speeding of the reaction as discussed above.

According to another improvement provided by the present invention, a ultraviolet radiation sensor 198 may be disposed so as to detect the intensity of ultraviolet radiation from the lamp 188. An output signal from sensor 198 may be used to compensate the rate of change of the $CO_2$ content, e.g., to make sequences of values recorded with respect to differing samples more directly comparable. For example, if two substantially identical water samples are analyzed using the instrument of the invention, but the lamp intensity is reduced by half in the second measurement with respect to the first, the shapes of the respective $CO_2$ content curves will normally be similar but the second will extend over double the extent of time. By monitoring the intensity of the UV radiation with sensor 198, one of the time sequences can be compensated so as to render such sequences of values directly comparable. The value for the intensity of the radiation detected by sensor 198 may also or alternatively be used in a feedback loop to control the power supplied by lamp power supply 200 to the lamp 188.

The actual analysis step is performed by a controller 202 which may be a conventional microprocessor-based computer or may be part of a larger data analysis system. The controller 202 may store the series of values received for subsequent analysis, and may archive the series of values for comparison to subsequent series of values. The conductivity/temperature electronics unit 192 may be integral with controller 202. The controller 202 receives the corrected conductivity values and converts these to values for the actual $CO_2$ content of the water sample. Where appropriate, the controller also employs a value for the pH of the sample measured by a pH sensor 204 prior to commencement of the UV exposure of the sample. Prior to commencement of the analysis a valve 206 is opened, flushing any water in the system therefrom until a fresh sample has been received. At that point the pH sensor 204 measures the pH of the water sample and the baseline values for the conductivity and temperature are made. If it is desired to measure the pH after completion of the oxidation reaction, the pH sensor 204 is exposed to the sample upon purging the sample cell to admit the next sample.

The output of the controller 202, including the final TOC value, is provided either on a display or by communication to another unit, as indicated generally at 208.

Therefore, while a preferred embodiment of the invention has been shown and described, it will be appreciated that numerous other modifications and improvements thereto will be suggested to those skilled in the art, and that these are considered to be within the scope of the invention. Accordingly, the invention should not be limited by the above exemplary disclosure, but only by the following claims.

We claim as our invention:

1. A method for measuring total organic carbon content of a sample of deionized water, comprising the steps of:
   introducing said sample of water to a sample cell, said cell comprising a window formed of a material transparent to ultraviolet radiation, and a pair of electrodes;
   irradiating said sample of water and said electrodes with ultraviolet radiation to oxidize the total organic carbon content of the sample of water to carbon dioxide;
   repetitively measuring the conductivity and temperature of said sample of water in said sample cell;
   employing the results of said repetitive measurements of the temperature and conductivity of the sample of water to yield a series of values for the carbon dioxide content of the sample of water; and
   analyzing said series of values to determine the initial total organic carbon content of the sample of water.

2. The method of claim 1 wherein said electrodes have surfaces of a material that catalyzes oxidation of organic compounds when irradiated with ultraviolet light, said electrode surfaces being arranged to be directly exposed to incident ultraviolet radiation.

3. The method of claim 1, further comprising the step of applying a voltage between said electrodes, whereby an electric field is created between said electrodes and electrophoresis causes ions in said sample of water to migrate towards said electrodes for oxidation.

4. The method of claim 1, wherein said step of analyzing said series of values to determine the initial total organic carbon content of said sample of water comprises the steps of monitoring the time-rate of change of the carbon dioxide content of said sample of water and determining when said time-rate of change is within a predetermined range around zero, indicating that said reaction has been completed.

5. The method of claim 1, wherein said step of analyzing said series of values to determine the initial total organic carbon content of said sample of water comprises the further steps of:
   employing a sequence of said series of values to determine the coefficients of an exponential relation expressing the carbon dioxide content of said sample of water as a function of time, said coefficients defining an asymptotic value for the carbon dioxide content of the sample of water upon oxidation of all organic carbon in said sample of water to carbon dioxide; and
   converting said asymptotic value for the carbon dioxide content of the sample of water to a value for the initial total organic carbon content of the sample of water.

6. The method of claim 1, comprising the further steps of measuring the pH of the sample of water prior to commencement of irradiation of said sample of water and following completion of said irradiation, and using said measured values of the pH of the sample of water to correct said series of values for the carbon dioxide content thereof.

7. A method for measuring the total organic carbon content of a sample of water, comprising the steps of:
   introducing said sample to a sample cell, said cell comprising a window formed of a material transparent to ultraviolet radiation, and including a material which when exposed to ultraviolet radiation catalyzes oxidation of organic species in water to carbon dioxide;
   irradiating said sample with ultraviolet radiation to oxidize organic carbon contained in the sample of water to carbon dioxide;
   repetitively measuring values of the conductivity and temperature of said sample of water; and
   analyzing said repetitively measured values of the conductivity and temperature of the sample of water to determine the initial total organic carbon content of the sample of water.

8. The method of claim 7 wherein said conductivity is measured between electrodes positioned so as to be capable of being exposed to said water sample, and having surfaces which comprise said material that catalyzes oxidation of organic compounds when irradiated with ultraviolet light, said electrode surfaces being arranged to be directly exposed to incident ultraviolet radiation.

9. The method of claim 8, further comprising the step of applying a voltage between said electrodes, whereby an electric field is created between said electrodes and electrophoresis causes ions in said water sample to migrate towards said electrodes for oxidation.

10. The method of claim 7, wherein said step of analyzing comprises the steps of monitoring the time-rate of change of the carbon dioxide content of said water sample and determining when said time-rate of change is within a predetermined range around zero, indicating that said reaction has been completed.

11. The method of claim 7, wherein said step of analyzing comprises the further steps of:
    employing a sequence of said values of the conductivity and temperature to determine the coefficients of an exponential relation expressing variation in the carbon dioxide content of said sample of water as a function of time, said coefficients defining an asymptotic value for the carbon dioxide content of the sample of water at completion of oxidation of organic carbon therein; and
    converting said asymptotic value for the carbon dioxide content of the sample of water to a value for the initial total organic carbon content of the sample of water.

12. The method of claim 11, comprising the further step of monitoring the intensity of ultraviolet radiation irradiating said sample of water.

13. The method of claim 12 wherein the monitored intensity of radiation is employed in said step of determining coefficients of an exponential relation to compensate the rate of change of the carbon dioxide content of the sample of water.

14. The method of claim 12, wherein the monitored intensity is employed in a control loop to maintain the intensity of ultraviolet radiation incident on the sample of water constant.

15. Apparatus for measurement of the total organic carbon content of a sample of water, comprising:
    a sample cell having a window;
    a source of ultraviolet radiation of a frequency which causes oxidation of organic carbon compounds in a water sample disposed in juxtaposition to said window, the material of said window being substantially transparent to said radiation;
    a pair of electrodes positioned so as to be capable of being exposed to said sample of water;

means for monitoring the electrical conductivity of said sample of water between said electrodes;

means in the vicinity of said electrodes for monitoring the temperature of said sample of water;

means for determining the equivalent carbon dioxide content of said sample of water as a function of the conductivity thereof, compensated responsive to the monitored temperature thereof;

means for monitoring variation in said equivalent carbon dioxide content of said sample of water as a function of time during which said sample of water is exposed to ultraviolet radiation from said source; and means for determining the total organic carbon content of said sample of water responsive to said monitored variation in said equivalent carbon dioxide content of said sample of water.

16. The apparatus of claim 15 further comprising means for determining when the equivalent carbon dioxide content or the time-rate of change of said equivalent carbon dioxide content has reached a stable value, indicating that oxidation of organic materials in said sample has been substantially completed.

17. The apparatus of claim 16, wherein said means for determining when said equivalent carbon dioxide content or the time-rate of change of said equivalent carbon dioxide content has reached a stable value comprises mean for monitoring first and second time derivatives of the equivalent carbon dioxide content between said electrodes and for determining when the second derivative of said equivalent carbon dioxide content is within a predetermined range about zero.

18. The apparatus of claim 15 wherein said means for determining the equivalent carbon dioxide content of said water as a function of the conductivity thereof performs said determination responsive to the assumption that said sample of water is deionized.

19. The apparatus of claim 15 wherein said means for determining the equivalent carbon dioxide content of said sample of water comprises means for measuring the pH of the water of said sample.

20. The apparatus of claim 15 wherein said pair of electrodes of said cell are arranged to be directly exposed to said ultraviolet radiation.

21. The apparatus of claim 20 wherein said electrodes comprise surfaces exposed to said ultraviolet radiation emitted by said source, said surfaces being photocatalytically active upon exposure to the ultraviolet radiation emitted by said source.

22. The apparatus of claim 21 wherein said photocatalytically active surfaces are of an N-type semiconductor.

23. The apparatus of claim 22 wherein said N-type semiconductor is titanium dioxide.

24. The apparatus of claim 23 wherein said source of radiation emits ultraviolet radiation at substantially 253.6 nanometers and 184.9 nanometers wavelength.

25. An apparatus for measuring total organic carbon contained in a sample of water, comprising:

a sample cell, said cell comprising a window formed of a material transparent to ultraviolet radiation, and containing at least one member of a catalyst material which when exposed to said ultraviolet radiation catalyzes oxidation of organic carbon in said water to carbon dioxide;

a source of ultraviolet radiation disposed in juxtaposition to said window, so as to irradiate a sample of water in said cell and said at least one member of a catalyst material with ultraviolet radiation;

means for monitoring the temperature of the sample of water;

means for measuring the conductivity of the sample of water; and means for correlating the measured conductivity of said sample of water to the equivalent organic carbon content of said sample of water responsive to the monitored temperature thereof.

26. The apparatus of claim 25 wherein said ultraviolet radiation includes a component substantially at 184.9 nm and a component at 253.6 nm wavelength.

27. The apparatus of claim 26 wherein said source of ultraviolet radiation is a low-pressure mercury vapor lamp.

28. The apparatus of claim 25, further comprising means for monitoring variation in the carbon dioxide content of said sample of water as a function of time, and for determining when the carbon dioxide content of said water reaches a stable value, indicating that said reaction has been completed.

29. The apparatus of claim 28, wherein said means for determining that the reaction has been completed comprises means for monitoring the time-rate of change of the carbon dioxide content of said water and for determining when the time-rate of change thereof has reached within a predetermined range of zero, indicating that said reaction has been completed.

30. The apparatus of claim 25 wherein said conductivity is measured using electrodes having surfaces which comprise said at least one member of a catalyst, and wherein said electrode surfaces are arranged to be directly exposed to incident ultraviolet radiation from said source.

31. The apparatus of claim 30, further comprising means for applying an electric potential to said electrodes, whereby an electric field is created between said electrodes and electrophoresis causes ions in said water stream to migrate towards said electrodes for oxidation.

32. The apparatus of claim 30 wherein said electrode surfaces are formed of an N-type semiconductor.

33. The apparatus of claim 32 wherein said semiconductor is titanium dioxide.

34. An apparatus for measuring total organic carbon contained in a sample of water, comprising:

a sample cell having a window formed of a material transparent to ultraviolet radiation therein;

a source of ultraviolet radiation disposed in juxtaposition to said window, for oxidizing organic carbon compounds in said water to carbon dioxide;

first and second electrodes in said cell;

means connected to said electrodes for repetitively measuring the conductivity of a water sample in said cell;

means for repetitively measuring the temperature of water in said cell;

means for converting a series of measured values of the conductivity of the sample of water, corrected responsive to the measured temperature thereof, to a series of values for the amount of carbon dioxide in the water sample; and means for analyzing said series of values for the amount of carbon dioxide in said sample of water to determine the total organic carbon content of said sample of water.

35. The apparatus of claim 34, wherein the surfaces of said electrodes are formed of a catalytic material, said electrode surfaces being arranged so as to be directly exposed to incident ultraviolet radiation from said source thereof.

36. The apparatus of claim 34 wherein said electrodes comprise a first annular outer electrode and a second circular inner electrode, said electrodes being mounted between said window and a planar member, said electrodes being spaced from one another to define an annular chamber between opposed surfaces thereof and said window and said planar member, and wherein said source of ultraviolet radiation comprises a generally circular active portion juxtaposed to said window opposite said annular chamber.

37. The apparatus of claim 34, further comprising means for analyzing variation in the determined carbon dioxide content of said sample of water, comprising means for comparing a series of values for the carbon dioxide content of the sample of water determined at predetermined intervals of time after commencement of exposure of the sample to ultraviolet radiation from said source to a comparable series of values determined with respect to a prior sample of water at like intervals after commencement of exposure of the prior sample to ultraviolet radiation from said source, and means for predicting the total organic carbon content of the sample prior to completion of the oxidation of organic carbon compounds therein.

38. The apparatus of claim 34, further comprising means for analyzing variation in the determined carbon dioxide content of said sample of water, comprising means for fitting a series of values for the carbon dioxide content of the sample of water to an exponential relation expressing the carbon dioxide content of the sample of water as a function of time, said relation approaching an asymptotic limit for the carbon dioxide content of the sample of water, means for determining said asymptotic limit, said limit being indicative of the carbon dioxide content of the sample of water upon complete oxidation of all organic carbon in the sample of water to carbon dioxide, and means for determining the total organic carbon content of the sample responsive to said asymptotic limit.

39. The apparatus of claim 34 wherein said catalytic material is an N-type semiconductor selected from the group consisting of $SrTiO_3$, $CdS$, $WO_3$, $Fe_2O_3$, $MO_3$ and $TiO_2$.

40. The apparatus of claim 39, wherein said material is $TiO_2$.

41. The apparatus of claim 34 wherein said source of ultraviolet radiation emits radiation including a component at substantially 184.9 nm wavelength and a component at substantially 253.6 nm wavelength.

42. The apparatus of claim 41 wherein said source of ultraviolet radiation is a low-pressure mercury vapor lamp.

43. In combination, the apparatus of claim 34 and means for measuring the pH of the sample of water.

44. The combination of claim 43 in further combination with means for determining the carbon dioxide content of said sample of water responsive to the measured values for the pH, conductivity and temperature thereof.

45. The combination of claim 44, further comprising means for analyzing the time-rate of change of the carbon dioxide content of a sample of water in said cell during irradiation of said sample of water by ultraviolet radiation from said source.

46. The combination of claim 45 wherein said means for analyzing comprises means for determining when said time-rate of change is within a predetermined range of zero, indicating that said oxidation of organic carbon compounds in said water sample has been completed.

* * * * *